US012570658B2

(12) United States Patent
Depre et al.

(10) Patent No.: US 12,570,658 B2
(45) Date of Patent: Mar. 10, 2026

(54) SYNTHETIC METHODS OF MAKING (2H-1, 2, 3-TRIAZOL-2-YL) PHENYL COMPOUNDS AS OREXIN RECEPTOR MODULATORS

(71) Applicant: JANSSEN PHARMACEUTICA NV, Beerse (BE)

(72) Inventors: Dominique Paul M Depre, Hamme-Mille (BE); Kiran Matcha, Turnhout (BE); Florian Damien Medina, Brussels (BE); Pieter Westerduin, Lichtaart (BE); Cheng Yi Chen, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 1069 days.

(21) Appl. No.: 17/633,407

(22) PCT Filed: Aug. 6, 2020

(86) PCT No.: PCT/EP2020/072192
§ 371 (c)(1),
(2) Date: Feb. 7, 2022

(87) PCT Pub. No.: WO2021/023843
PCT Pub. Date: Feb. 11, 2021

(65) Prior Publication Data

US 2022/0289754 A1 Sep. 15, 2022

Related U.S. Application Data

(60) Provisional application No. 62/971,265, filed on Feb. 7, 2020, provisional application No. 62/883,857, filed on Aug. 7, 2019.

(51) Int. Cl.
*C07D 487/04* (2006.01)
*C07C 249/16* (2006.01)
*C07C 251/76* (2006.01)
*C07C 251/78* (2006.01)
*C07D 249/06* (2006.01)

(52) U.S. Cl.
CPC .......... *C07D 487/04* (2013.01); *C07C 249/16* (2013.01); *C07C 251/76* (2013.01); *C07C 251/78* (2013.01); *C07D 249/06* (2013.01)

(58) Field of Classification Search
CPC .................................................... C07D 487/04
See application file for complete search history.

(56) References Cited

U.S. PATENT DOCUMENTS 4,233,440 A 11/1980 Dorlars et al.
4,826,833 A 5/1989 Chen
8,653,263 B2 2/2014 Chai et al.
2002/0019388 A1 2/2002 Schrimpf et al.
2005/0065178 A1 3/2005 Basha et al.
2005/0101602 A1 5/2005 Basha et al.
2006/0258672 A1 11/2006 Barbosa et al.
2011/0313003 A1 12/2011 Shi et al.
2012/0208812 A1 8/2012 Chai et al.
2013/0137672 A1 5/2013 Branstetter et al.
2014/0171430 A1 6/2014 Letavic et al.
2015/0239847 A1 8/2015 Heilmann et al.
2017/0258790 A1 9/2017 De Boer et al.
2017/0320874 A1 11/2017 Kim et al.
2018/0155333 A1 6/2018 Kamei et al.

FOREIGN PATENT DOCUMENTS

CN 102781942 A 11/2012
CN 103012293 A 4/2013
EP 3287454 A1 2/2018
JP 49-083724 A 8/1974
JP 2015-535843 A 12/2015
TW 201141859 A 12/2011
WO 95/15327 A1 6/1995
WO 2001/081347 A2 11/2001
WO 2006/123121 A1 11/2006
WO 2006/124897 A2 11/2006
WO 2008/067121 A2 6/2008
WO 2009/081197 A1 7/2009

(Continued)

OTHER PUBLICATIONS

Chen, Cheng-yi, et al. “Synthesis of 2-Substituted 1,2,3-Triazoles via an Intramolecular N—N Bond Formation.” Eur. J. Org. Chem. (2020), pp. 548-551. (Year: 2020).*
“Benzoic acid, 2-fluro-6-(2H-1,2,3-triazol-2-yl)-, methyl ester,” CAS Registry No. 2114143-60-9, Database Registry 2017, p. 1.
CID 123365637, PubChem 2017, https://pubchem.ncbi.nlm.nih.gov/compound/ “2-(3-Fluorophenyl) triazole,” pp. 12.
PubChem CID 108125092, (3aR,6aS)-5-(4,6-dimethylpyrimidin-2-yl)-2,3,3a,4,6,6a-hexahydro-1H-pyrrolo[3,4-c]pyrrole, Jan. 15, 2016, 10 Pages.
PubChem CID 124416753, (3aS,6aS)-2-benzyl-5-pyrimidin-2-yl-1,3,3a,4,6,6a-hexahydropyrrolo[3,4-c]pyrrole, Apr. 10, 2017, 9 Pages.
“Monocyclic 2-Substituted 1,2,3-Triazoles”, Science of Synthesis, Section 13.13.2, 2004, pp. 528-540.

(Continued)

*Primary Examiner* — John S Kenyon
(74) *Attorney, Agent, or Firm* — BakerHostetler

(57) ABSTRACT

Processes for preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

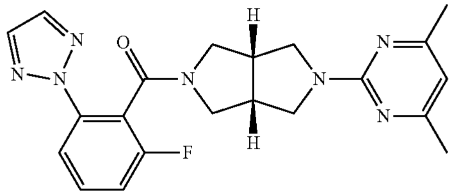

are described, which are useful for commercial manufacturing. Said compound is an orexin receptor modulator and may be useful in pharmaceutical compositions and methods for the treatment of diseased states, disorders, and conditions mediated by orexin activity, such as insomnia and depression.

9 Claims, No Drawings

(56) References Cited

FOREIGN PATENT DOCUMENTS

| | | | |
|---|---|---|---|
| WO | 2014/053450 | A1 | 4/2014 |
| WO | 2015/150252 | A1 | 10/2015 |
| WO | 2018/146466 | A1 | 8/2018 |

OTHER PUBLICATIONS

Belskaya et al., "Synthesis of 2H-1,2,3-Triazoles", Topics Heterocycl. Chem., 2015, vol. 40, pp. 51-116.
Frost et al., "Synthesis and Structure-Activity Relationships of 3,8-Diazabicyclo[4.2.0]octane Ligands, Potent Nicotinic Acetylcholine Receptor Agonists", Journal of Medicinal Chemistry, 2006, vol. 49 No. 26, pp. 7843-7853.
Green et al., "Protective Groups in Organic Synthesis", Wiley-Interscience, New York, 1999, pp. 579-580 & 744-747.
Huang et al., "Practical Asymmetric Synthesis of RO5114436, a CCR5 Receptor Antagonist", Organic Process Research & Development, Oct. 3, 2010, vol. 14, Issue 3, pp. 592-599.
Joucla et al., "Parent and N-substituted azomethine ylides from a-amino acids and formaldehyde: An easy access to 2,5-unsubstituted pyrrolidines. Evidence for oxazolidin-5-ones as direct precursor of these reactive intermediates", Bulletin de la Societe Chimique de France, 1988, vol. 1988, Issue 3, pp. 579-583.
Letavic et al., "Novel Octahydropyrrolo[3,4-c]pyrroles Are Selective Orexin-2 Antagonists: SAR Leading to a Clinical Candidate", J. Med. Chem., 2015, vol. 58, Issue 14, pp. 5620-5636.
Manka et al., "Octahydropyrrolo[3,4-c]pyrrole Negative Allosteric Modulators of mGlu1", Bioorg Med Chem Lett., 2013, vol. 23, Issue 18, pp. 5091-5096.
McAlpine et al., "Synthesis of Small 3-Fluoro- and 3,3-Difluoropyrrolidines Using Azomethine Ylide", Chemistry. J. Org. Chem., 2015, vol. 80, No. 14, pp. 7266-7274.
Myachina, "Optimization of the synthesis of 2-phenyl-1,2,3-triazole", Chemistry of Heterocyclic Compounds, 2010, vol. 46 No. 1, pp. 79-81.
Oldham, "5-Oxazolidinones: Key Intermediates to Peptidomimetics with Latent Reactivity and Conformational Restriction," Doctoral Thesis, University of Canterbury, 1997, pp. 1-63.
Peyron et al., "Neurons Containing Hypocretin (Orexin) Project to Multiple Neuronal Systems", J. Neurosci., 1998, vol. 18 No. 23, pp. 9996-10015.
Potkin et al., "Synthesis of 3-amino-4,5-dichloroisothiazole", Russian Journal of Organic Chemistry, Dec. 2009, vol. 45 No. 4, pp. 555-558.
Pubchem CID 101510576, pp. 1-7, Create Date: Dec. 18, 2015.
Pubchem CID 128564374, pp. 1-6, Create Date: Jun. 18, 2017.
Pubchem CID 1514449, pp. 1-11, Create Date: Jul. 11, 2005.
Pubchem CID 21867682, pp. 1-11, Create Date: Dec. 5, 2007.
Pubchem CID 312674, pp. 1-13, Create Date: Mar. 26, 2005.
Pubchem CID 59486002, pp. 1-8, Create Date: Aug. 20, 2012.
Riebsomer, "2-Phenyl-2,1,3-Triazole and Derivatives", J. Org. Chem., 1948, vol. 13, pp. 815-821.
Roth et al., "Highly Selective Synthesis of 2-(2H-1,2,3-Triazol-2-yl)benzoic Acids", OPRD 2019, vol. 23, pp. 234-243.
Talapatra et al, "Synthesis of Heterocycles. I: N-Iodosuccinimide, A Convenient Oxidative Cyclising Agent in the Synthesis of Oxazole, Isoxazole, Benzofuran, Furoxan and 1,2,3-Triazole-1-Oxide Derivatives", Heterocycles, 1980, vol. 14 No. 9, pp. 1279-1282.
Tsuge et al., "Simple Generation of Nonstabilized Azomethine Ylides Through Decarboxylative Condensation of a-Amino Acids with Carbonyl Compounds via 5-Oxazolidinone Intermediates", Bulletin of the Chemical Society of Japan, Nov. 1987, vol. 60, Issue 11, pp. 4079-4089.
Ueda et al., "Highly N2-Selective Palladium-Catalyzed Arylation of 1,2,3-Triazoles", Angew. Chem. Int. Ed., 2011, vol. 50 No. 38, pp. 8944-8947.
Van Den Pol et al., "Hypothalamic Hypocretin (Orexin): Robust Innervation of the Spinal Cord", J. Neuroscience, 1999, vol. 19 No. 8, pp. 3171-3182.
Wang et al., "Highly Regioselective N-2 Arylation of 4,5-Dibromo-1,2,3-triazole: Efficient Synthesis of 2-Aryltriazoles", Org. Let., 2009, vol. 11 No. 21, pp. 5026-5028.
RN: 1941655-07-7, "Pyrrolo[3,4-c]pyrrole-1,3(2H,3aH)-dione, 5-(4,6-diethyl-2-pyrimidinyl)tetrahydro-, (3aR,6aS)", Chemcats, Jun. 29, 2016, 1 page.
"2-Fluoro-6-(2H-1,2,3-triazol-2-yl)benzoic acid", PubChem CID 67086627, https://pubchem.ncbi.nlm.nih.gov/compound/67086627, Nov. 30, 2012, pp. 1-13.
Boss et al., "Substituted cyclopentanes, tetrahydrofurans and pyrrolidines as orexin-1-receptor antagonists for treatment of various CNS disorders (WO2015/055994; WO2015/124932; WO2015/124934)", Expert Opinion on Therapeutic Patents, vol. 26, No. 3 Dec. 2015, pp. 409-415.
Miao et al., "Progress in the study of orexin receptor antagonists" Tianjin Pharmacy, vol. 29, No. 5, Oct. 28, 2017, pp. 69-73.
Miao-Miao et al., "Orexins in regulation of sleep and awakening", Academic Journal of Second Military Medical University, No. 05, May 30, 2004, 544-546.
Shen et al., "3-aminopyrazolopyrazine derivatives as spleen tyrosine kinase inhibitors", Chem Biol Drug Des, May 14, 2016, vol. 88, pp. 690-698.

* cited by examiner

SYNTHETIC METHODS OF MAKING (2H-1, 2, 3-TRIAZOL-2-YL) PHENYL COMPOUNDS AS OREXIN RECEPTOR MODULATORS

CROSS REFERENCE TO RELATED APPLICATIONS

The present U.S. Patent Application is a U.S. National Phase Application under 35 U.S.C. 371 of International Application PCT/EP2020/072192 filed on Aug. 6, 2020, which claims the benefit of U.S. provisional patent application No. 62/883,857 filed Aug. 7, 2019 and U.S. provisional patent application No. 62/971,265, filed Feb. 7, 2020, all of which are incorporated by reference herein in their entireties.

FIELD OF THE INVENTION

The present invention relates to the synthesis methods making (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone (Seltorexant), a compound useful for modulation of the orexin receptor and for the treatment of disease states, disorders, and conditions mediated by orexin receptor activity.

BACKGROUND OF THE INVENTION

Orexin (or hypocretin) signaling is mediated by two receptors and two peptide agonists. The two orexin peptides (orexin A and orexin B) herein after referred to as orexins, bind to two high affinity receptors, termed orexin-1 and orexin-2 receptors. The orexin-1 receptor is selective in favor of orexin A, while the orexin-2 receptor binds both orexins with similar affinities. The orexins, are cleavage products of the same gene, prepro orexin. In the central nervous system neurons expressing prepro-orexin, the precursor from which orexin is produced, are found in the perifornical nucleus, the dorsal hypothalamus and the lateral hypothalamus (C. Peyron et al., *J. Neurosci.,* 1998, 18(23), 9996-10015). Orexinergic cells in these nuclei project to many areas of the brain, extending rostrally to the olfactory bulbs and caudally to the spinal cord (van den Pol, A. N. et al., *J. Neuroscience.,* 1999, 19(8), 3171-3182).

Citation of a reference herein shall not be construed as an admission that such reference is prior art to the present invention. All publications referred to herein are incorporated by reference in their entireties.

Substituted diaza-bicyclic compounds have been reported as active central nervous system agents (International Publication No. WO2001081347, Nov. 1, 2001; US2002/0019388, Feb. 14, 2002), □□7 acetylcholine receptor modulators (US2005/101602, May 12, 2005; US2005/0065178, Mar. 24, 2005 and Frost et al, *Journal of Medicinal Chemistry,* 2006, 49(26), 7843-7853), proline transporter inhibitors for the treatment of cognitive impairment (WO2008067121, Jun. 5, 2008) and for improving cognition (WO 2006 124897, Nov. 23, 2006 and US20060258672, Nov. 16, 2006), as androgen receptor ligands for the treatment of androgen receptor associated conditions including cancer (WO2009081197, Jul. 2, 2009), and as histone deacetylase inhibitors for the treatment of cancers, neurodegenerative diseases and autoimmune diseases (WO20060123121, Nov. 23, 2006).

Among the developed compounds, (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone was found to act as an inhibitor of the orexin-2 receptor and to be useful for the treatment of sleep disorders and major depressive diseases (U.S. Pat. No. 8,653,263 B2). The compound was assembled from two key building blocks as shown in Scheme 1 below:

Scheme 1

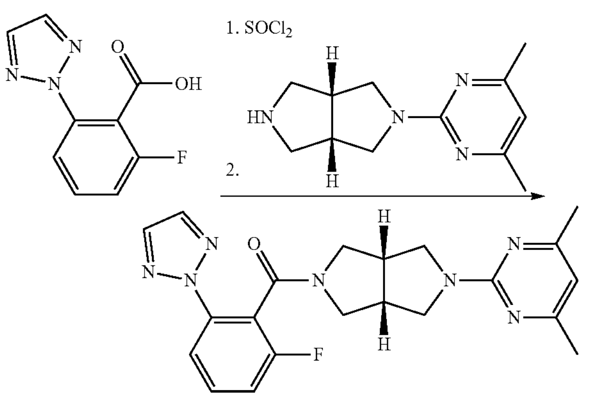

The original synthesis employed a direct phenyl-to-triazole coupling. A mixture of products resulted from unselective coupling to the different nitrogen atoms on the triazole, as shown in Scheme 2 below.

Scheme 2

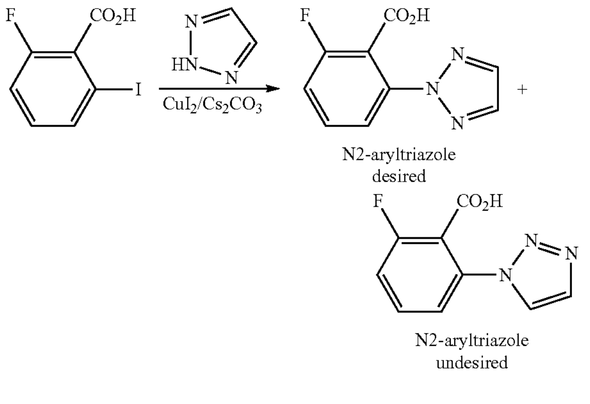

Exclusive synthesis of 2-aryltriazoles can be accomplished by means of Cu(II) mediated bis-hydrazone cyclization, as shown in Scheme 3. However, the approach suffers from poor atom economy, since bis-addition of the phenylhydrazine to glyoxal results in 50% of the aryl building block being converted to aniline-by product (see for instance *J. Org. Chem.* 1948, 13, 815; for recent improvements to the dihydrazone approach, see *Russian Journal of Organic Chemistry* 2009, 45, 1683; and *Chemistry of Heterocyclic Compounds* 2010, 46, 79).

Scheme 3

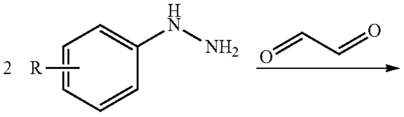

-continued

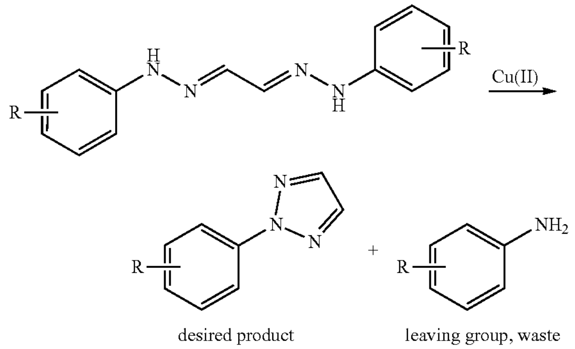

Other efforts to make the 2-substituted triazoles have been reported (Tomé, A. C. *Science of Synthesis* 2004, *Section* 13.13.2, pp 528-540; *Topics Heterocycl. Chem.* 2015, 40, 51; *Org. Let.* 2009, 11, 5026; OPRD 2019, 23, 234; *Angew. Chem. Int. Ed.* 2011, 50, 8944; and *Heterocycles* 1980, 14, 1279.) but in all cases, approaches through cyclization of intermediates to 2-aryltriazole derivatives suffer from low yield when the positions 4 and 5 of the triazole ring are unsubstituted.

It is an object of the invention to provide a process for preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone utilizing exclusive N2-aryl-triazole production in order to reduce waste, to eliminate the need for separating the undesired coupling product, and to reduce the manufacturing cost.

SUMMARY OF THE INVENTION

The invention comprises a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

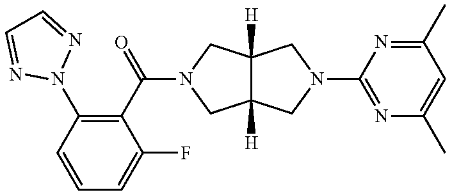 [SMILES: Cc1cc(C)nc(N2C[C@H]3CN(C(=O)c4c(F)cccc4-n4nccn4)C[C@H]3C2)n1]

said process comprising the step described below:

cyclization of the hydrazone of Formula I to give the 2-phenyl-2H-1,2,3-triazole of Formula II in a single step

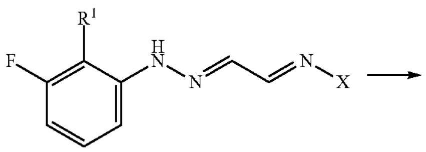

I

-continued

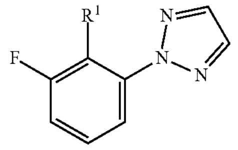

II wherein $R^1$ is —H, —$CO_2H$, or —$CO_2C_{(1-4)}$alkyl;

X is —OH, —$OC_{(1-4)}$alkyl, —$OCH_2Ph$, —OPh, —OC(O)$CH_3$, —$OSO_2CH_3$, —$N(CH_3)_2$, piperidin-1-yl, —NHC(O)$CH_3$, —$NHSO_2PhCH_3$, or —$N(CH_3)_3I$.

DETAILED DESCRIPTION OF THE INVENTION

The invention comprises a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

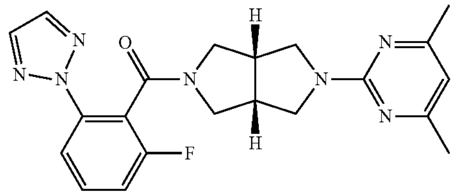 [SMILES: Cc1cc(C)nc(N2C[C@H]3CN(C(=O)c4c(F)cccc4-n4nccn4)C[C@H]3C2)n1]

said process comprising the step described below:

cyclization of the hydrazine of Formula I to give the 2-phenyl-2H-1,2,3-triazole of Formula II in a single step

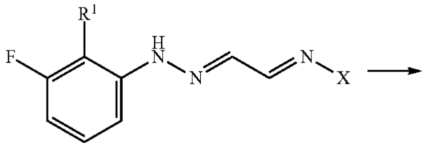

I

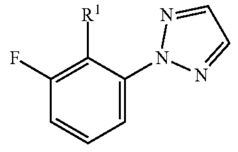

II wherein $R^1$ is —H, —$CO_2H$, or —$CO_2C_{(1-4)}$alkyl;

X is —OH, —$OC_{(1-4)}$alkyl, —$OCH_2Ph$, —OPh, —OC(O)$CH_3$, —$OSO_2CH_3$, —$N(CH_3)_2$, piperidin-1-yl, —NHC(O)$CH_3$, —$NHSO_2PhCH_3$, or —$N(CH_3)_3I$.

In Another Embodiment of the Invention:

The invention comprises a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

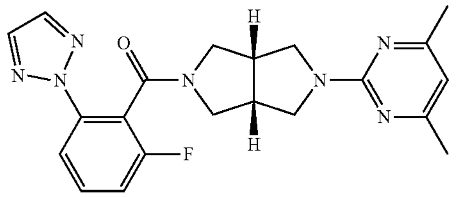 [SMILES: Cc1cc(C)nc(N2C[C@H]3CN(C(=O)c4c(F)cccc4-n4nccn4)C[C@H]3C2)n1]

said process comprising the step described below:

cyclization of the hydrazine of Formula I to give the 2-phenyl-2H-1,2,3-triazole of Formula II in a single step

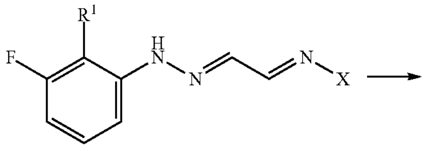

I

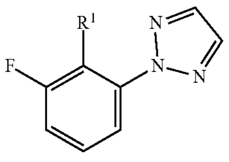

II wherein $R^1$ is —H, or —$CO_2CH_3$;

X is —$OC_{(1-2)}$alkyl, —$OC(CH_3)_3$, —$OCH_2Ph$, —$N(CH_3)_2$, or —$N(CH_3)_3I$.

In Another Embodiment of the Invention:

The invention comprises a process of preparing (((3aR, 6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

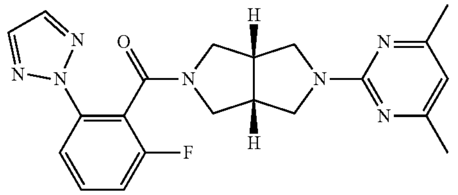 [SMILES: Cc1cc(C)nc(N2C[C@H]3CN(C(=O)c4c(F)cccc4-n4nccn4)C[C@H]3C2)n1]

said process comprising the steps described below:

a) cyclization of the hydrazine of Formula I to give the 2-phenyl-2H-1,2,3-triazole of Formula II in a single step

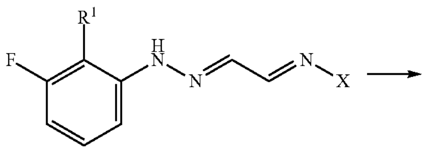

I

-continued

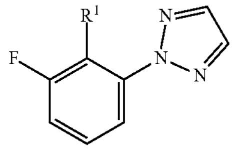

II wherein $R^1$ is —H;

X is —$OC_{(1-2)}$alkyl, —$OC(CH_3)_3$, —$OCH_2Ph$, —$N(CH_3)_2$, or —$N(CH_3)_3I$.

b) carboxylation of 2-(3-fluorophenyl)-2H-1,2,3-triazole to give 2-fluoro-6-(2H-1,2,3-triazol-2-yl)benzoic acid,

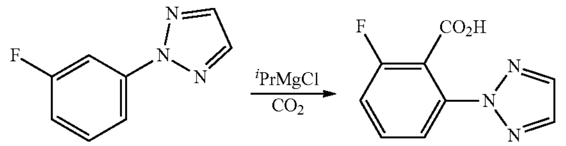

wherein said carboxylation is characterized by the use of isopropyl-MgCl and $CO_2$.

In Another Embodiment of the Invention:

The invention comprises a process of preparing (((3aR, 6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

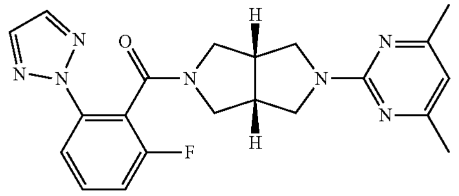 [SMILES: Cc1cc(C)nc(N2C[C@H]3CN(C(=O)c4c(F)cccc4-n4nccn4)C[C@H]3C2)n1]

said process comprising the steps described below:

a) cyclization of the hydrazine of Formula I to give the 2-phenyl-2H-1,2,3-triazole of Formula II in a single step

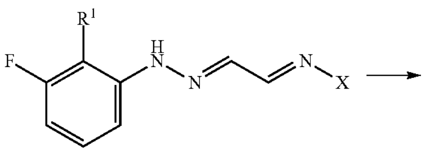

I

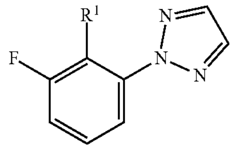

II wherein $R^1$ is —H;

X is —$OC_{(1-2)}$alkyl, —$OC(CH_3)_3$, —$OCH_2Ph$, —$N(CH_3)_2$, or —$N(CH_3)_3I$;

b) carboxylation of 2-(3-fluorophenyl)-2H-1,2,3-triazole to give 2-fluoro-6-(2H-1,2,3-triazol-2-yl)benzoic acid,

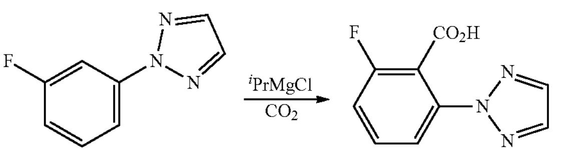

wherein said carboxylation is characterized by the use of isopropyl-MgCl and $CO_2$;

c) Reaction of 2-fluoro-6-(2H-1,2,3-triazol-2-yl)benzoic acid with (3aR,6aS)-2-(4,6-dimethylpyrimidin-2-yl)octahydropyrrolo[3,4-c]pyrrole to form (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

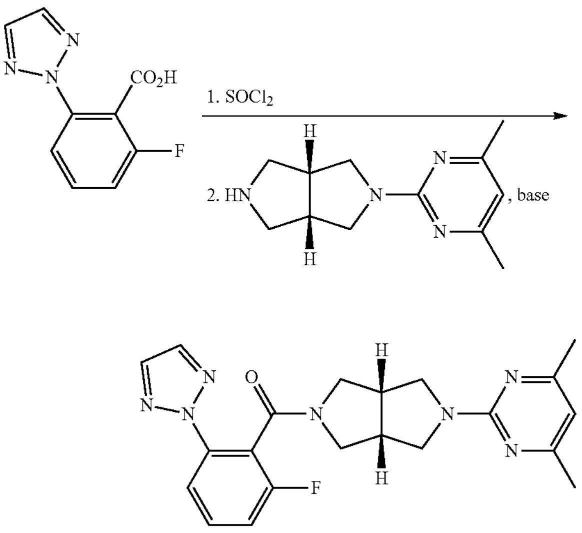

wherein said reaction is characterized by the use of $SOCl_2$.

In Another Embodiment of the Invention:

The invention comprises a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

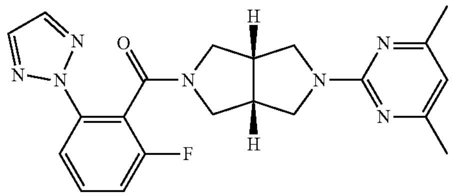 [SMILES: Cc1cc(C)nc(N2C[C@H]3CN(C(=O)c4c(F)cccc4-n4nccn4)C[C@H]3C2)n1]

said process comprising the steps described below:

a) cyclization of the hydrazine of Formula I to give the 2-phenyl-2H-1,2,3-triazole of Formula II in a single step

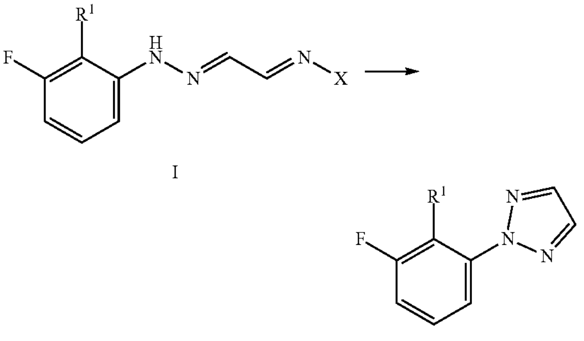

I

II wherein $R^1$ is —H;

X is —$OC_{(1-2)}$alkyl, —$OC(CH_3)_3$, —$OCH_2Ph$, —$N(CH_3)_2$, or —$N(CH_3)_3I$;

b) carboxylation of 2-(3-fluorophenyl)-2H-1,2,3-triazole to give 2-fluoro-6-(2H-1,2,3-triazol-2-yl)benzoic acid,

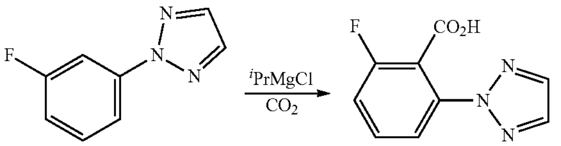

wherein said carboxylation is characterized by the use of LiCl, isopropyl-MgCl and $CO_2$;

c) Reaction of 2-fluoro-6-(2H-1,2,3-triazol-2-yl)benzoic acid with (3aR,6aS)-2-(4,6-dimethylpyrimidin-2-yl)octahydropyrrolo[3,4-c]pyrrole to form (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

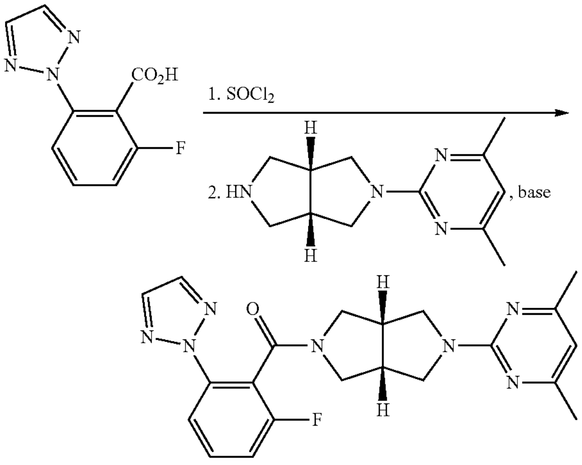

wherein said reaction is characterized by the use of $SOCl_2$.

The invention also comprises a method of making a compound of Formula I

I

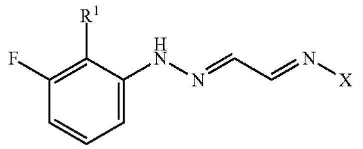

said method comprises

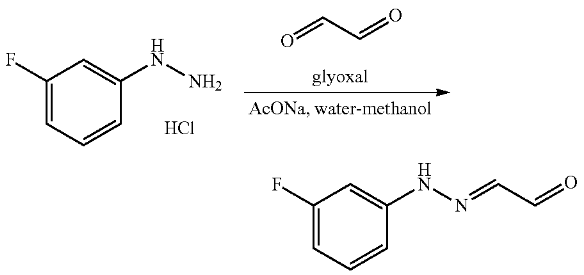

reaction of (3-fluorophenyl)hydrazine hydrochloride with glyoxal, in the presence of water and/or methanol, to form (E)-2-(2-(3-fluorophenyl)hydrazono)acetaldehyde in over 90% yield;

wherein $R^1$ is H, $CO_2H$, or —$CO_2C_{(1-4)}$alkyl;

and

X is —OH, —$OC_{(1-4)}$alkyl, —$OCH_2Ph$, —OPh, —OAc, —$N(CH_3)_2$, piperidinyl, —$NHC(O)CH_3$, —$NHSO_2PhCH_3$, or —$N(CH_3)_3I$.

Another embodiment of the invention is a compound of Formula I:

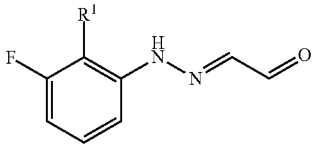

wherein $R^1$ is H, $CO_2H$, or —$CO_2C_{(1-4)}$alkyl.

Another embodiment of the invention is a compound selected from the group consisting of:

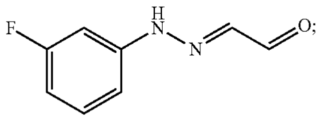

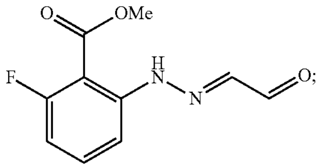

and

-continued

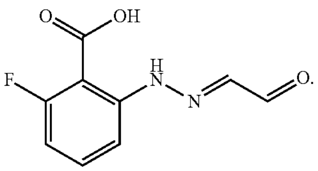

Another embodiment of the invention is a compound selected from the group consisting of:

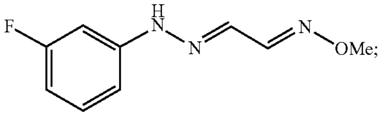

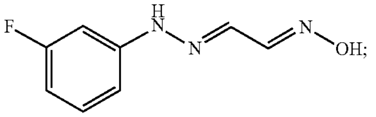

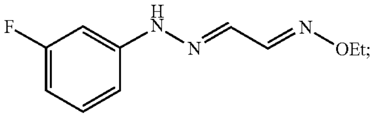

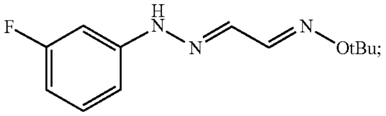

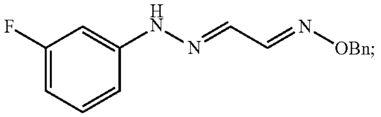

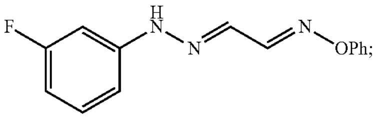

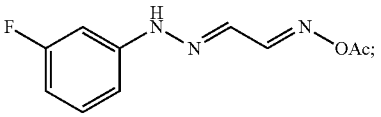

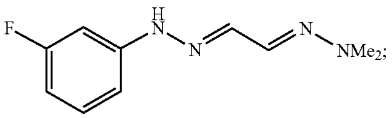

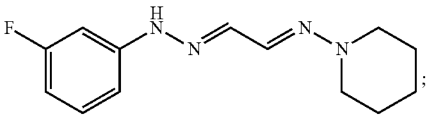

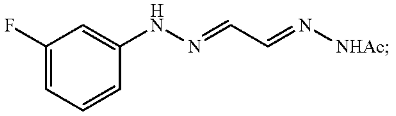

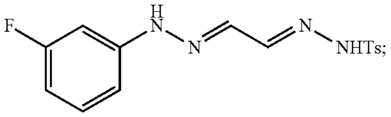

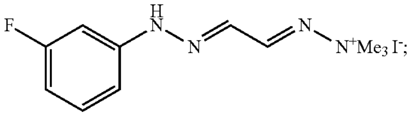

-continued

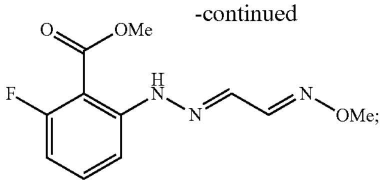

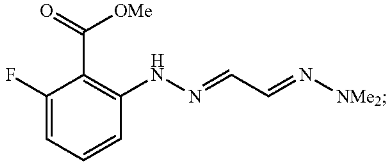

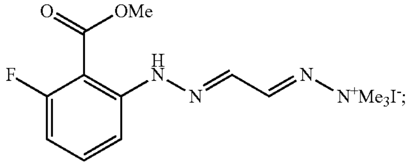

and

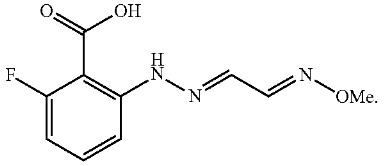 [SMILES: CO/N=C/C=N/Nc1cccc(F)c1C(=O)O]

Another embodiment of the invention is a compound selected from the group consisting of:

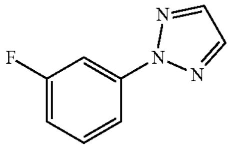

; and

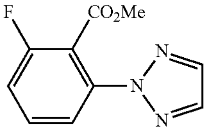

.

The invention may be more fully appreciated by reference to the following description, including the following glossary of terms and the concluding examples. For the sake of brevity, the disclosures of the publications, including patents, cited in this specification are herein incorporated by reference.

As used herein, the terms “including”, “containing” and “comprising” are used herein in their open, non-limiting sense.

Definitions

The term “(((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone” means

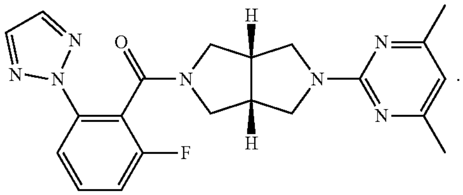 [SMILES: Cc1cc(C)nc(N2C[C@H]3CN(C(=O)c4c(F)cccc4-n4nccn4)C[C@H]3C2)n1]

.

Products of the chemical reactions described in this specification may be reacted directly with additional reagents or may be separated prior to subsequent reaction. The term “isolated” means the partial or complete separation of a reaction product from other materials in the reaction vessel. These other materials include, but are not limited to solvents, unreacted starting material, reagents used in the reaction, side-products, impurities and the products of reagents used in the reaction.

The term “preparing” means synthesizing by means of chemical processes.

Additionally, any formula given herein is intended to refer also to hydrates, solvates, and polymorphs of such compounds, and mixtures thereof, even if such forms are not listed explicitly.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, fluorine, and chlorine, such as $^{2}H$, $^{3}H$, $^{11}C$, $^{13}C$, $^{14}C$, $^{15}N$, $^{18}O$, $^{17}O$, respectively. Such isotopically labeled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Those skilled in the art will recognize that compounds of the invention, where at least one double bond is present, may exist as stereoisomers. The invention contemplates both (E) and (Z) stereoisomers and all mixtures thereof.

Those skilled in the art will recognize that compounds and reagents used in the reactions of the invention may exist as salts. The invention contemplates the use of all salts of any compound used in a reaction exemplified herein.

Examples of salts include, without limitation, sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When a compound or reagent used in a reaction of the invention contains a basic nitrogen, a salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

Those skilled in the art will recognize many reagents may be used for the saponification of an ester

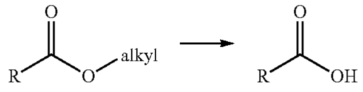

and those reagents are both diverse and known to the skilled practitioner. The invention contemplates the use of all common means of ester conversion to carboxylic acid, including those described in *Protective Groups in Organic Synthesis*, by T. W. Green, and P. G. M. Wuts, Wiley-Interscience, New York, 1999, 579-580, 744-747.

Exemplary reactions useful in methods of the invention will now be described by reference to the illustrative synthetic schemes for their general preparation below and the specific examples that follow. Those skilled in the art will recognize that reactions may be performed in any suitable solvent. Those skilled in the art will also recognize that, except where specifically limited, reactions may be performed at a wide range of temperatures. Unless otherwise specified, reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations

Herein and throughout the specification, the flowing abbreviations may be used.

| Abbreviation | Term |
|---|---|
| Ac | acetyl |
| ACN | acetonitrile |
| Bn | benzyl |
| DCM | dichloromethane |
| DMSO | dimethylsulfoxide |
| EG | ethylene glycol |
| EtOAc, or EA | ethyl Acetate |
| Et | ethyl |
| HPLC | high-performance liquid chromatography |
| iPr or $^{i}$Pr | isopropyl |
| LC | liquid chromatography |
| Me | methyl |
| nBu or $^{n}$Bu | n-butyl |
| OAc | acetate |
| OTf | triflate (=trifluoromethanesulfonyl) |
| Ph | phenyl |
| tBu or $^{t}$Bu | tert-butyl |
| THF | tetrahydrofuran |
| Ts | tosyl (=p-toluenesulfonyl) |

EXAMPLES

In obtaining the compounds described in the examples below and the corresponding analytical data, the following experimental and analytical protocols were followed unless otherwise indicated.

Unless otherwise stated, reaction mixtures were stirred at room temperature (rt) under a nitrogen atmosphere. Where mixtures, solutions, and extracts were "concentrated", they were typically concentrated under reduced pressure. Reactions under microwave irradiation conditions were carried out in a Biotage Initiator or CEM Discover instrument.

Normal-phase flash column chromatography (FCC) was performed on silica gel ($SiO_2$) using prepackaged cartridges, eluting with the indicated solvents.

Mass spectra (MS) were obtained on either Bruker QTOF, Waters QTOF Ultima instruments using electrospray ionization (ESI) in positive mode unless otherwise indicated, or on a Waters GC-TOF using electronic impact (EI). Calculated (calcd.) mass corresponds to the exact mass.

Nuclear magnetic resonance (NMR) spectra were obtained on Bruker spectrometers. The format of the $^{1}$H NMR data below is: chemical shift in ppm downfield of the tetramethylsilane reference (multiplicity, coupling constant J in Hz, integration).

Chemical names were generated using ChemDraw Ultra 6.0.2 (CambridgeSoft Corp., Cambridge, MA) or ACD/Name Version 9 (Advanced Chemistry Development, Toronto, Ontario, Canada).

GENERAL SCHEME

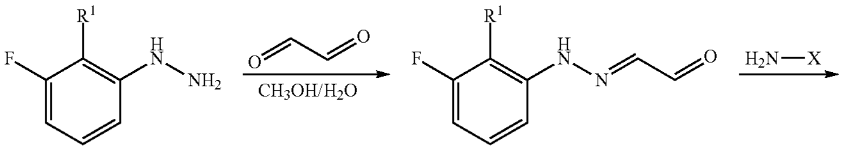

III IV

-continued

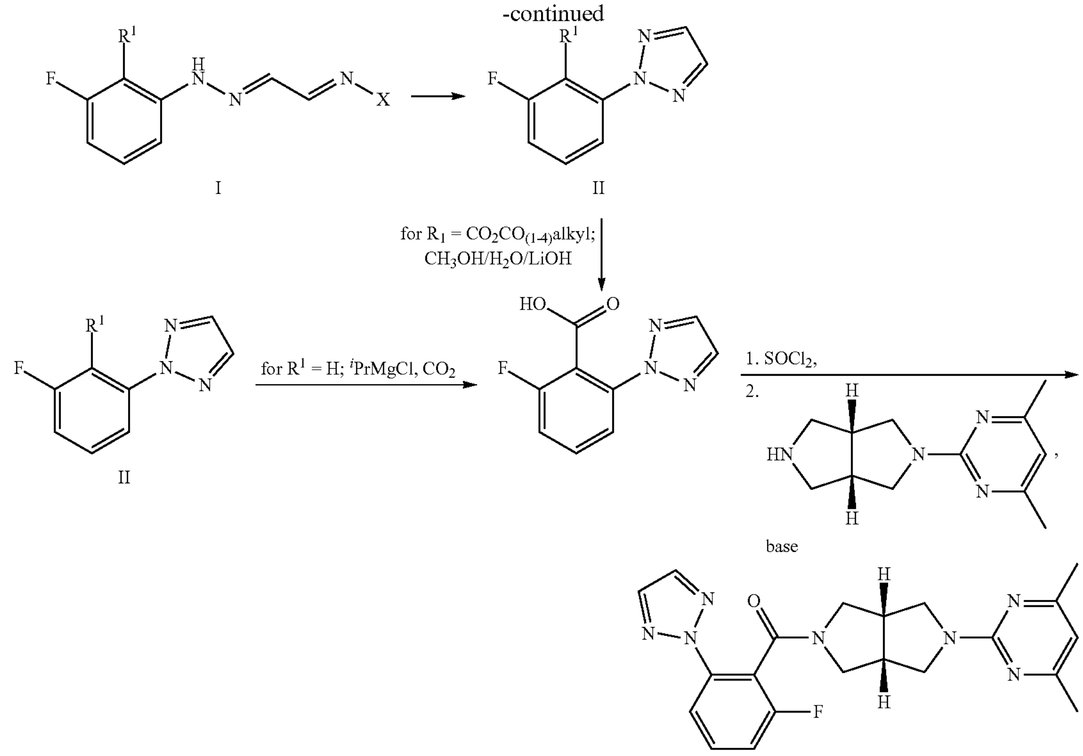

Phenyl hydrazines III or corresponding salts in the presence of sodium acetate may be reacted with glyoxal and water or water-methanol to form hydrazonoacetaldehyde IV. The present invention uses a water-glyoxal mixture in which the phenyl hydrazine is sparingly soluble, to accomplish the desired mono-condensation with a relatively small excess of glyoxal. The desired mono condensation product may be obtained in high yield by an appropriate solvent, such as water, or a mixture of methanol and water, which minimizes the concentration of hydrazine starting material in solution, and also allows the product of mono condensation product to precipitate out of solution as it is formed.

Condensation with $H_2N$—X affords the hydrazone I. The product is formed as a mixture of E/Z stereoisomers which interconvert upon heating; there is no need to separate the stereoisomers from each other. Cyclization of the hydrazone mixture gives the 2-phenyl-2H-1,2,3-triazole II in a single step from I.

Elaboration of the 2-phenyl-2H-1,2,3-triazole II is accomplished by means of saponification when $R^1$ is —$CO_2C_{(1-4)}$alkyl, or carboxylation when $R^1$ is H, gives 2-fluoro-6-(2H-1,2,3-triazol-2-yl)benzoic acid. Addition of LiCl to the reaction mixture reduced undesired bis-addition of —$CO_2$.

The product 2-fluoro-6-(2H-1,2,3-triazol-2-yl)benzoic acid is activated using thionyl chloride or any suitable activating agent, and reacted with (3aR,6aS)-2-(4,6-dimethylpyrimidin-2-yl)octahydropyrrolo[3,4-c]pyrrole to form ((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone.

Example 1: Synthesis of Hydrazonoacetaldehydes of Formula IV

Example 1a: Synthesis of (E)-2-(2-(3-fluorophenyl)hydrazono)acetaldehyde

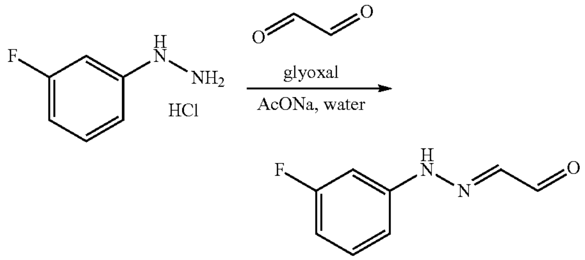

A 40 w/w % solution of glyoxal in water (613 g, 4.22 mol) was added to a suspension of 177 g (1.06 mol) of (3-fluorophenyl)hydrazine (HCl salt) in 1.24 L of water followed by the addition of a solution of 129.9 g (1.58 mol) of sodium acetate in 708 mL of water over 2 hours. After a few hours stirring at room temperature, the suspension was filtered, and the cake was washed with 0.89 L of water and dried under vacuum to deliver 172.8 g (95% yield) of the title compound as a yellow solid.

mp 118-119° C.

$^1H$ NMR (DMSO-$d_6$) δ: 11.80 (br s, 1H), 9.49 (d, J=7.7 Hz, 1H), 7.36 (d, J=7.9 Hz, 1H), 7.32-7.39 (m, 1H), 6.96-7.03 (m, 2H), 6.75-6.83 (m, 1H). $^{13}C$ NMR (DMSO-$d_6$) δ: 190.4, 163.0 (br d, J=242.7 Hz), 144.7 (br d, J=10.8 Hz), 136.3, 131.2 (d, J=10.0 Hz), 110.0 (d, J=2.3 Hz), 108.5 (d, J=21.6 Hz), 100.6 (d, J=27.0 Hz). $^{19}F$ NMR (DMSO-$d_6$) δ: −111.72.

HRMS (ESI-TOF) m/z: $[M+H]^+$ Calcd for $C_8H_8FN_2O$ 167.0621. Found 167.0611.

Example 1b: Synthesis of methyl (E)-2-fluoro-6-(2-(2-oxoethylidene)hydrazinyl)benzoate

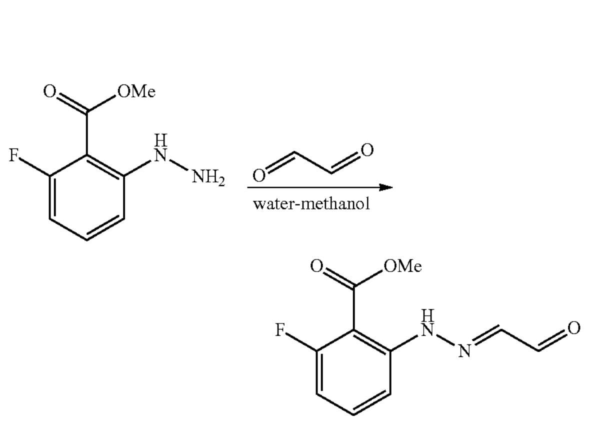

A solution of methyl 2-fluoro-6-hydrazinylbenzoate (17.65 g, 0.08 mol) in methanol-water (90 ml+180 ml) was added at 10° C. over 10 minutes to a mixture of 40 w % solution of glyoxal in water (58.04 g, 0.8 mol), water (100 ml) and sodium acetate (9.85 g, 0.12 mol). The mixture was then stirred for ca 1.5 h before filtration. The filter cake was rinsed with water (2×50 ml) and dried under vacuum. The dried solid (16.12 g) was redissolved at 50° C. in ethyl acetate (50 ml) before crystallization by slow addition of heptane (200 ml) and cooling to 5° C. The resulting solid was filtered, rinsed with heptane (2×15 ml) and dried under vacuum. The desired product (13.33 g, 74% yield) was obtained as a yellow solid. mp 110.8° C.

$^1H$ NMR (DMSO-$d_6$) δ: 11.74 (s, 1H), 9.41 (d, 1H), 7.49 (m, 2H), 7.19 (d, 1H), 6.92 (m, 1H), 3.84 (s, 3H).

MS (ESI-TOF) m/z: 225.1 ($[M+H]^+$).

Example 1c: Synthesis of (E)-2-fluoro-6-(2-(2-oxoethylidene)hydrazinyl)benzoic acid

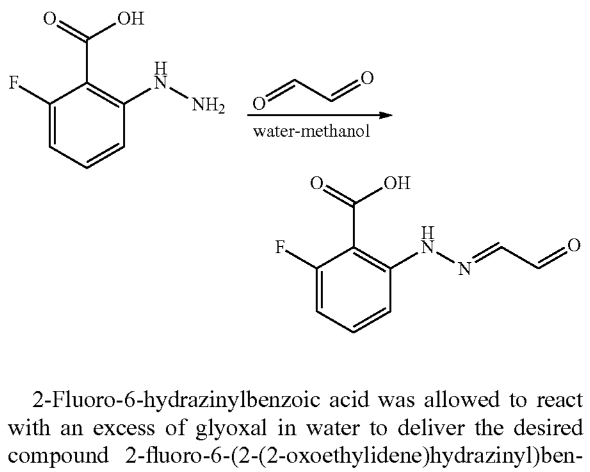

2-Fluoro-6-hydrazinylbenzoic acid was allowed to react with an excess of glyoxal in water to deliver the desired compound 2-fluoro-6-(2-(2-oxoethylidene)hydrazinyl)benzoic acid in 64% yield as a yellow solid. the compound was used as such in the next step.

Example 2: Synthesis of Hydrazones of Formula I

Example 2a: Synthesis of (1E,2E)-2-(2-(3-fluorophenyl)hydrazono)acetaldehyde O-methyl oxime

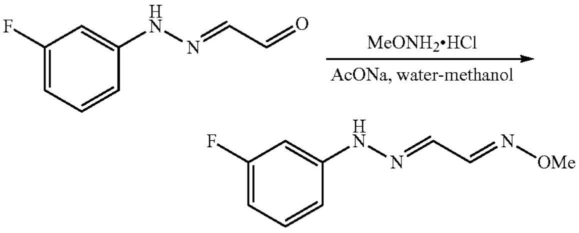

A solution of 59.7 g (715 mmol) of methoxylamine hydrochloride and 58.6 g (715 mmol) of sodium acetate in 210 mL of water was added to a solution of 70 g (408 mmol) of (E)-2-(2-(3-fluorophenyl)hydrazono)acetaldehyde in 350 mL of methanol over 1.5 hours, followed by the addition of 210 mL of water. After 2 hours stirring at room temperature, the suspension was cooled to 0° C. and stirred overnight at this temperature before filtration. The filter cake was washed with 70 mL of water and dried under vacuum to deliver 77.4 g (92% yield) of the title compound as a yellow solid. NMR analysis revealed the presence of 2 isomers (~1/1 ratio). Separation of the Isomers.

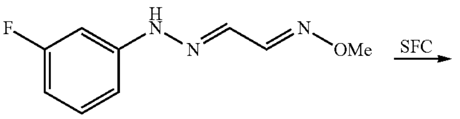

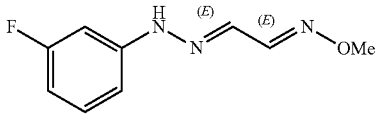

+ isomer 1

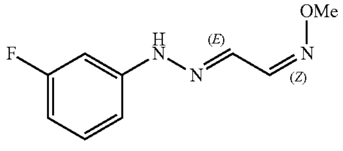

isomer 2

Isomers of 10 g of the reaction product of Example 2a were separated by supercritical fluid chromatography (SFC—eluent: isocratic 7% acetonitrile in supercritical $CO_2$) to give 6 g (63% yield) of isomer 1 (E,E) and 2.7 g (28% yield) of isomer 2 (E,Z).

Isomer 1 (E,E):

mp: 90° C.

$^1H$ NMR (DMSO-$d_6$) δ: 10.89 (s, 1H), 7.83 (d, J=8.8 Hz, 1H), 7.54 (dd, J=8.8, 0.7 Hz, 1H), 7.20-7.28 (m, 1H), 6.74-6.83 (m, 2H), 6.54-6.62 (m, 1H), 3.84 (s, 3H). $^{13}C$ NMR (DMSO-$d_6$) δ: 163.2 (br d, J=241.2 Hz), 148.3, 146.1 ((br d, J=10.8 Hz), 132.8, 130.8 (d, J=10.0 Hz), 108.4 (d, J=2.3 Hz), 105.9 (d, J=21.6 Hz), 98.9 (d, J=27.0 Hz), 61.7. $^{19}F$ NMR (DMSO-$d_6$) δ: −112.30.

HRMS (ESI-TOF) m/z: $[M+H]^+$ Calcd for $C_9H_{11}FN_3O$ 196.0881. Found 196.0876.

Isomer 2 (E,Z):

mp 114° C.

$^{1}$H NMR (DMSO-$d_6$) δ: 11.04 (s, 1H), 7.96 (dd, J=8.6, 0.9 Hz, 1H), 7.25 (d, J=8.4 Hz, 1H), 7.21-7.29 (m, 1H), 6.78-6.86 (m, 2H), 6.59-6.66 (m, 1H), 3.85 (s, 3H). $^{13}$C NMR (DMSO-$d_6$) δ=163.2 (br d, J=242.0 Hz), 145.8 (br d, J=10.8 Hz), 145.4, 130.8 (d, J=10.0 Hz), 127.9, 108.8 (d, J=2.3 Hz), 106.6 (d, J=21.6 Hz), 99.3 (d, J=26.2 Hz), 61.7. $^{19}$F NMR (DMSO-$d_6$) δ: −112.18.

HRMS (ESI-TOF) m/z: $[M+H]^+$ Calcd for $C_9H_{11}FN_3O$ 196.0881. Found 196.0876.

Example 2b: Alternative Synthesis of (1E,2E)-2-(2-(3-fluorophenyl)hydrazono)acetaldehyde O-methyl oxime from Compound (3-fluorophenyl)hydrazine (HCl salt), glyoxal and methoxylamine HCl without Drying (E)-2-(2-(3-fluorophenyl)hydrazono) acetaldehyde A first reactor was charged with 4.5 kg of (3-fluorophenyl)hydrazine (HCl salt) and 36 L of water. The suspension was stirred at 65° C. for an hour. A second reactor was charged with 6.15 kg of glyoxal and 4.6 L of water and cooled to 10° C. the aqueous solution of (3-fluorophenyl) hydrazine (HCl salt) was transferred from the first reactor to the second reactor over 2 hours. The reaction mixture was further stirred for 3 hours before filtration and wash of the solid (E)-2-(2-(3-fluorophenyl)hydrazono)acetaldehyde with water. The wet cake was recharged in the reactor together with 18 kg of methanol. 3.77 kg of hydroxylamine HCl, 3.7 kg of sodium acetate and 9 kg of water are then added with efficient stirring. The suspension was stirred for 30-60 min, 18 kg of water was added, and the final mixture was cooled to 5° C. and stirred for 1-2 hours. The mixture of products (1E,2E)-2-(2-(3-fluorophenyl)hydrazono)acetaldehyde O-methyl oxime and (1E,2Z)-2-(2-(3-fluorophenyl)hydrazono)acetaldehyde O-methyl oxime was filtered, washed with water and dried under vacuum to deliver 5.01 kg of yellow solid (yield: 93%) with >99% purity.

Example 2c: Synthesis of Compounds of Formula I from (E)-2-(2-(3-fluorophenyl)hydrazono)acetaldehyde and X—$NH_2$

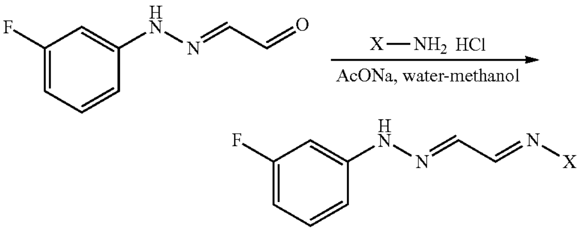

Unless mentioned, compounds of Formula I wherein $R^1$ is H were prepared from (E)-2-(2-(3-fluorophenyl)hydrazono) acetaldehyde and X—$NH_2$ following the procedure for Example 2a, or very similar procedure, and either used crude or purified by crystallization or by chromatography. Results are reported in Table 1.

TABLE 1

| X-$NH_2$ | 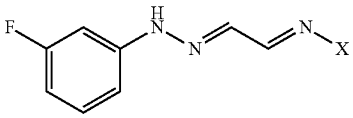 | % yield | isomeric ratio (2 to 4 isomers observed) |
|---|---|---|---|
| HO—$NH_2$ HCl | 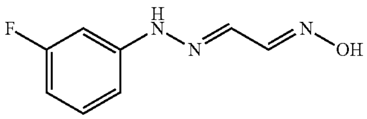 | 71 | 85/15 |
| EtO—$NH_2$•HCl | 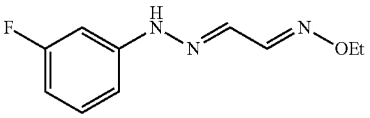 [SMILES: CCO/N=C/C=N/Nc1cccc(F)c1] | 91 | 76/24 |
| $^t$BuO—$NH_2$•HCl | 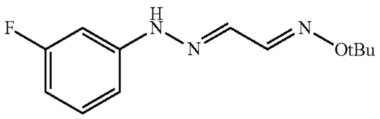 [SMILES: CC(C)(C)O/N=C/C=N/Nc1cccc(F)c1] | 80 | 74/18/10/4 |
| BnO—$NH_2$•HCl | 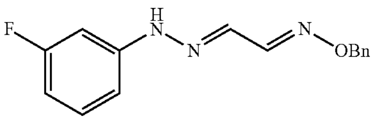 | 79 | 95/5 |
| PhO—$NH_2$•HCl | 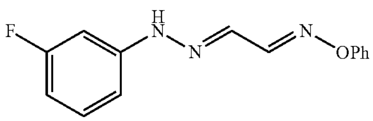 [SMILES: Fc1cccc(N/N=C/C=N/OCc2ccccc2)c1] | 99 | 67/33 |

TABLE 1-continued

| X-$NH_2$ | 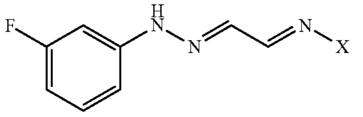 | % yield | isomeric ratio (2 to 4 isomers observed) |
|---|---|---|---|
| HO—$NH_2$•HCl then $Ac_2O$ | 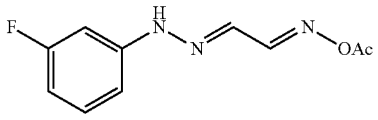 | 65 | 86/10/4 |
| $Me_2N$—$NH_2$ | 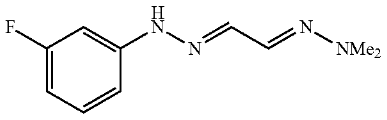 | 89 | Single isomer |
| 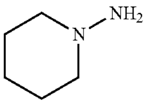 | 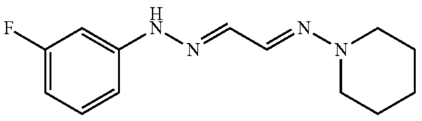 [SMILES: Fc1cccc(N/N=C/C=N/N2CCCCC2)c1] | 90 | Single isomer |
| AcNH—$NH_2$ | 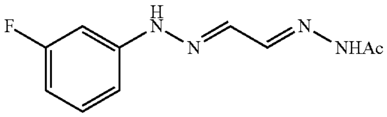 [SMILES: CC(=O)N/N=C/C=N/Nc1cccc(F)c1] | 53 | <95/>5 (major isomer shows rotamerization) |
| TsNH—$NH_2$ | 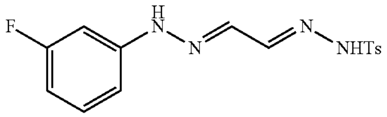 | 85 | Single isomer |
| $Me_2N$—$NH_2$ Then MeI | 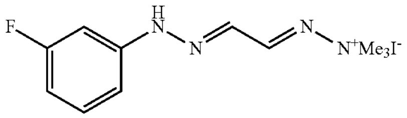 | 90 | Single isomer |

(1E,2E)-2-(2-(3-fluorophenyl)hydrazono)acetaldehyde oxime

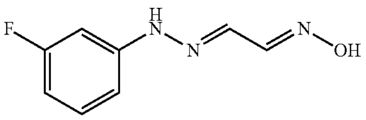

Yellow solid. mp 135° C.

Isomer 1 (major): $^1$H NMR (400 MHz, DMSO-$d_6$) δ=11.33 (s, 1H), 10.70 (s, 1H), 7.77 (d, J=8.6 Hz, 1H), 7.59 (dd, J=0.4, 8.8 Hz, 1H), 7.27-7.17 (m, 1H), 6.80-6.76 (m, 1H), 6.75 (d, J=1.5 Hz, 1H), 6.59-6.51 (m, 1H). $^{13}$C NMR (101 MHz, DMSO-$d_6$) δ=163.24 (br d, J=241.2 Hz), 147.88, 146.46 (br d, J=10.8 Hz), 134.44, 130.74 (d, J=10.0 Hz), 108.29 (d, J=2.3 Hz), 105.56 (d, J=21.6 Hz), 98.71 (d, J=26.2 Hz). $^{19}$F NMR (377 MHz, DMSO-$d_6$) δ=−112.36.

HRMS (ESI-TOF) m/z: $[M+H]^+$ Calcd for $C_8H_9FN_3O$ 182.0730. Found 182.0726.

Isomer 2 (minor): $^1$H NMR (400 MHz, DMSO-$d_6$) δ=11.28 (s, 1H), 10.90 (s, 1H), 8.06 (dd, J=0.7, 8.4 Hz, 1H), 7.27-7.17 (m, 2H), 6.83-6.80 (m, 1H), 6.80-6.76 (m, 1H), 6.63-6.59 (m, 1H). $^{13}$C NMR (101 MHz, DMSO-$d_6$) δ=163.21 (br d, J=241.2 Hz), 146.16 (br d, J=10.8 Hz), 144.96, 130.82 (d, J=10.0 Hz), 128.71, 108.65 (d, J=2.3 Hz), 106.14 (d, J=21.6 Hz), 99.09 (d, J=26.2 Hz). $^{19}$F NMR (377 MHz, DMSO-$d_6$) δ=−112.26.

HRMS (ESI-TOF) m/z: $[M+H]^+$ Calcd for $C_8H_9FN_3O$ 182.0730. Found 182.0727.

(1E,2E)-2-(2-(3-fluorophenyl)hydrazono)acetaldehyde O-ethyl oxime

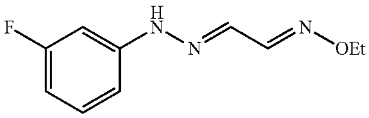 [SMILES: CCO/N=C/C=N/Nc1cccc(F)c1]

Yellow solid. mp: 82.7 and 101.7° C. (mixture of isomers).

Isomer 1 (major): $^1$H NMR (400 MHz, DMSO-$d_6$) δ=10.88 (s, 1H), 7.82 (d, J=8.6 Hz, 1H), 7.56 (d, J=8.8 Hz, 1H), 7.29-7.18 (m, 1H), 6.85-6.73 (m, 2H), 6.61-6.52 (m, 1H), 4.10 (q, J=7.0 Hz, 2H), 1.22 (t, J=7.0 Hz, 3H). $^{13}$C NMR (101 MHz, DMSO-$d_6$) δ=163.21 (br d, J=241.2 Hz), 148.02, 146.20 (br d, J=10.8 Hz), 133.08, 130.73 (d, J=10.0 Hz), 108.40 (d, J=2.3 Hz), 105.84 (d, J=20.8 Hz), 98.86 (d, J=26.2 Hz), 69.24, 14.31. $^{19}$F NMR (377 MHz, DMSO-$d_6$) δ=−112.34.

HRMS (ESI-TOF) m/z: $[M+H]^+$ Calcd for $C_{10}H_{13}FN_3O$ 210.1043. Found 210.1035.

Isomer 2 (minor): $^1H$ NMR (400 MHz, DMSO-$d_6$) δ=11.05 (s, 1H), 8.00 (d, J=8.6 Hz, 1H), 7.29-7.18 (m, 2H), 6.85-6.73 (m, 2H), 6.66-6.58 (m, 1H), 4.11 (q, J=7.0 Hz, 2H), 1.22 (br t, J=7.0 Hz, 3H). $^{13}C$ NMR (101 MHz, DMSO-$d_6$) δ=163.16 (br d, J=241.2 Hz), 145.86 (br d, J=11.6 Hz), 145.17, 130.80 (br d, J=10.0 Hz), 128.15, 108.78 (d, J=2.3 Hz), 106.46 (d, J=21.6 Hz), 99.25 (d, J=27.0 Hz), 69.20, 14.38. $^{19}F$ NMR (377 MHz, DMSO-$d_6$) δ=−112.22.

HRMS (ESI-TOF) m/z: $[M+H]^+$ Calcd for $C_{10}H_{13}FN_3O$ 210.1043. Found 210.1035.

(1E,2E)-2-(2-(3-fluorophenyl)hydrazono)acetaldehyde O-(tert-butyl) oxime

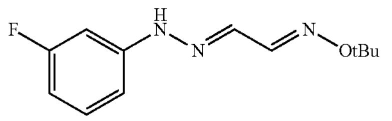 [SMILES: CC(C)(C)O/N=C/C=N/Nc1cccc(F)c1]

Yellow solid. mp: 93.8° C. (mixture of isomers).

Isomer 1: $^1H$ NMR (400 MHz, DMSO-$d_6$) δ=10.80 (s, 1H), 7.80 (d, J=8.6 Hz, 1H), 7.60 (d, J=9.0 Hz, 1H), 7.29-7.18 (m, 1H), 6.84-6.75 (m, 2H), 6.60-6.53 (m, 1H), 1.28 (s, 9H). $^{13}C$ NMR (101 MHz, DMSO-$d_6$) δ=163.23 (br d, J=241.2 Hz), 147.19, 146.33 (br d, J=10.8 Hz), 133.76, 130.63 (d, J=10.0 Hz), 108.35 (d, J=2.3 Hz), 105.66 (d, J=21.6 Hz), 98.84 (d, J=26.2 Hz), 78.78, 27.18. $^{19}F$ NMR (377 MHz, DMSO-$d_6$) δ=−112.36.

HRMS (ESI-TOF) m/z: $[M+H]^+$ Calcd for $C_{12}H_{17}FN_3O$ 238.1356. Found 238.1351.

Isomer 2: $^1H$ NMR (400 MHz, DMSO-$d_6$) δ=11.02 (s, 1H), 8.03 (d, J=9.0 Hz, 1H), 7.29-7.18 (m, 2H), 6.84-6.75 (m, 2H), 6.60-6.53 (m, 1H), 1.29 (s, 9H). $^{13}C$ NMR (101 MHz, DMSO-$d_6$) δ=163.18 (br d, J=242.0 Hz), 146.01 (br d, J=10.8 Hz), 144.37, 130.69 (br d, J=10.0 Hz), 128.56, 108.70 (d, J=2.3 Hz), 99.17 (d, J=26.2 Hz), 78.40, 27.18. $^{19}F$ NMR (377 MHz, DMSO-$d_6$) δ=−112.29.

HRMS (ESI-TOF) m/z: $[M+H]^+$ Calcd for $C_{12}H_{17}FN_3O$ 238.1356. Found 238.1351.

Isomer 3: $^1H$ NMR (400 MHz, DMSO-$d_6$) δ=10.93 (s, 1H) 7.80 (m, 1H), 6.89 (m, 1H), 7.29-7.18 (m, 1H), 6.84-6.75 (m, 2H), 6.60-6.53 (m, 1H), 1.34 (s, 9H). $^{13}C$ NMR (101 MHz, DMSO-$d_6$) δ=163.30 (br d, J=241.2 Hz), 146.66 (d, J=11.6 Hz), 141.90, 137.58, 130.69 (br d, J=10.0 Hz, 1C), 130.63 (d, J=10.0 Hz, 1C), 130.56 (d, J=10.0 Hz, 1C), 128.56, 127.44, 108.13 (d, J=2.3 Hz), 105.04 (d, J=21.6 Hz), 98.49 (d, J=26.2 Hz), 79.63, 27.11. $^{19}F$ NMR (377 MHz, DMSO-$d_6$) δ=−112.16.

HRMS (ESI-TOF) m/z: $[M+H]^+$ Calcd for $C_{12}H_{17}FN_3O$ 238.1356. Found 238.1351.

Isomer 4: $^1H$ NMR (400 MHz, DMSO-$d_6$) δ=11.35 (s, 1H), 8.28 (d, J=6.8 Hz, 1H), 7.29-7.18 (m, 1H), 6.84-6.75 (m, 3H), 6.60-6.53 (m, 1H), 1.27 (s, 9H). $^{13}C$ NMR (101 MHz, DMSO-$d_6$-detected signals) δ=163.30 (br d, J=241.2 Hz, 1C), 163.23 (br d, J=241.2 Hz, 1C), 163.18 (br d, J=242.0 Hz, 1C), 144.28, 127.44, 108.86 (d, J=2.3 Hz), 106.56 (d, J=21.6 Hz), 99.38 (br d, J=26.2 Hz), 27.06. $^{19}F$ NMR (377 MHz, DMSO-$d_6$) δ=−112.22.

(1E,2E)-2-(2-(3-fluorophenyl)hydrazono)acetaldehyde O-benzyl oxime

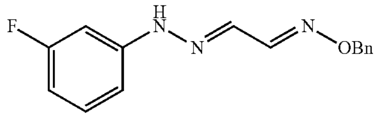 [SMILES: Fc1cccc(N/N=C/C=N/OCc2ccccc2)c1]

Yellow solid. mp: 105.6° C. (mixture of isomers).

Isomer 1 (major): $^1H$ NMR (400 MHz, DMSO-$d_6$) δ=10.91 (s, 1H), 7.94 (d, J=8.8 Hz, 1H), 7.56 (d, J=9.0 Hz, 1H), 7.42-7.27 (m, 5H), 7.27-7.19 (m, 1H), 6.87-6.76 (m, 2H), 6.62-6.54 (m, 1H), 5.13 (s, 1H). $^{13}C$ NMR (101 MHz, DMSO-$d_6$) δ=163.20 (d, J=241.2 Hz), 148.86, 146.13 (br d, J=10.8 Hz, 1C), 137.43, 132.71, 130.74 (d, J=9.2 Hz), 128.25, 128.00, 127.74, 108.46 (d, J=2.3 Hz), 105.96 (d, J=21.6 Hz), 98.95 (d, J=26.2 Hz), 75.51. $^{19}F$ NMR (377 MHz, DMSO-$d_6$) δ=−112.23.

HRMS (ESI-TOF) m/z: $[M+H]^+$ Calcd for $C_{15}H_{15}FN_3O$ 272.1199. Found 272.1198.

Isomer 2 (minor): $^1H$ NMR (400 MHz, DMSO-$d_6$) δ=11.08 (s, 1H), 8.06 (d, J=9.0 Hz, 1H), 7.56 (d, J=9.0 Hz, 1H), 7.42-7.27 (m, 5H), 7.27-7.19 (m, 1H), 6.87-6.76 (m, 2H), 6.66-6.62 (m, 1H), 5.14 (br s, 1H). $^{13}C$ NMR (101 MHz, DMSO-$d_6$) δ=163.16 (br d, J=241.2 Hz), 145.94, 137.50, 108.83 (d, J=2.3 Hz), 106.58 (d, J=21.6 Hz), 99.31 (d, J=26.2 Hz) 75.56. $^{19}F$ NMR (377 MHz, DMSO-$d_6$) δ=−112.12.

HRMS (ESI-TOF) m/z: $[M+H]^+$ Calcd for $C_{15}H_{15}FN_3O$ 272.1199. Found 272.1199.

Isomer 3: HRMS (ESI-TOF) m/z: $[M+H]^+$ Calcd for $C_{15}H_{15}FN_3O$ 272.1199. Found 272.1200.

(1E,2E)-2-(2-(3-fluorophenyl)hydrazono)acetaldehyde O-phenyl oxime

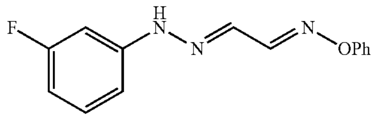 [SMILES: Fc1cccc(N/N=C/C=N/Oc2ccccc2)c1]

Yellow solid. mp: 93.4° C. (mixture of isomers).

Isomer 1 (major): $^1H$ NMR (400 MHz, DMSO-$d_6$) δ=11.17 (s, 1H), 8.28 (d, J=8.6 Hz, 1H), 7.70 (d, J=8.8 Hz, 1H), 7.45-7.32 (m, 2H), 7.32-7.23 (m, 1H), 7.18 (d, J=7.9 Hz, 2H), 7.09-7.01 (m, 1H), 6.93-6.81 (m, 2H), 6.64 (dt, J=2.2, 8.6 Hz, 1H). $^{13}C$ NMR (101 MHz, DMSO-$d_6$) δ=163.17 (br d, J=241.2 Hz), 158.61, 151.99, 145.82 (br d, J=11.6 Hz), 131.57, 130.87 (d, J=9.2 Hz), 129.44, 122.43, 114.18, 108.72 (d, J=2.3 Hz), 106.48 (d, J=21.6 Hz), 99.62 (d, J=26.2 Hz). $^{19}F$ NMR (377 MHz, DMSO-$d_6$) δ=−112.13.

HRMS (ESI-TOF) m/z: $[M+H]^+$ Calcd for $C_{14}H_{13}FN_3O$ 258.1043. Found 258.1038.

Isomer 2 (minor): $^1H$ NMR (400 MHz, DMSO-$d_6$) δ=11.38 (s, 1H), 8.19 (d, J=8.6 Hz, 1H), 7.69 (br d, J=8.4 Hz, 1H), 7.45-7.32 (m, 2H), 7.32-7.23 (m, 1H), 7.18 (d, J=7.9 Hz, 2H), 7.09-7.01 (m, 1H), 6.93-6.81 (m, 2H), 6.69 (dt, J=2.2, 8.6 Hz, 1H). $^{13}C$ NMR (101 MHz, DMSO-$d_6$) δ=163.13 (br d, J=242.0 Hz), 158.66, 148.82, 145.47 (br d, J=10.8 Hz), 130.95 (d, J=10.0 Hz), 129.44, 127.23, 122.33, 114.21, 109.14 (d, J=2.3 Hz), 107.14 (d, J=21.6 Hz), 99.62 (d, J=26.2 Hz). $^{19}F$ NMR (377 MHz, DMSO-$d_6$) δ=−112.02.

HRMS (ESI-TOF) m/z: $[M+H]^+$ Calcd for $C_{14}H_{13}FN_3O$ 258.1043. Found 258.1038.

(1E,2E)-2-(2-(3-fluorophenyl)hydrazono)acetaldehyde O-acetyl oxime

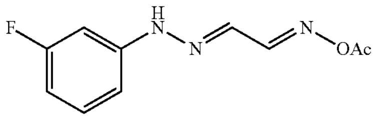 [SMILES: CC(=O)O/N=C/C=N/Nc1cccc(F)c1]

1.16 ml of 50 w % aqueous solution of hydroxylamine (19 mmol) was added to a solution of 3 g (18 mmol) of compound (E)-2-(2-(3-fluorophenyl)hydrazono)acetaldehyde in 15 ml of methanol. After overnight stirring at room temperature, 3.6 ml (19 mmol) of acetic anhydride was added on two portions. After overnight stirring, 15 ml of water was added to complete the precipitation. The desired compound was filtered, washed with a few ml of water and dried under vacuum to deliver 2.6 g (65% yield) of a yellow solid.

Yellow solid. mp: 100.8° C. (mixture of isomers).

Isomer 1:

$^1H$ NMR (400 MHz, DMSO-$d_6$) δ=11.31 (br s, 1H), 8.20 (d, J=8.8 Hz, 1H), 7.63 (d, J=8.8 Hz, 1H), 7.36-7.22 (m, 1H), 6.93-6.79 (m, 2H), 6.78-6.60 (m, 1H), 2.15 (s, 3H). $^{13}C$ NMR (101 MHz, DMSO-$d_6$) δ=167.88, 163.15 (br d, J=242.0 Hz), 155.53, 145.54 (br d, J=10.8 Hz), 131.12 (d, J=10.0 Hz), 130.58, 108.93 (d, J=2.3 Hz), 106.94 (d, J=21.6 Hz), 99.44 (d, J=26.2 Hz), 19.25. $^{19}F$ NMR (377 MHz, DMSO-$d_6$) δ=−112.07.

HRMS (ESI-TOF) m/z: $[M+H]^+$ Calcd for $C_{10}H_{11}FN_3O_2$ 224.0835. Found 224.0835.

Isomer 2:

$^1H$ NMR (400 MHz, DMSO-$d_6$, visible signals) δ=11.46 (br s, 1H), 7.36-7.22 (m, 1H), 6.99 (s, 1H), 6.93-6.79 (m, 2H), 6.78-6.60 (m, 1H), 1.91 (s, 3H). $^{13}C$ NMR (101 MHz, DMSO-$d_6$) δ=171.93, 163.02 (br d, J=242.7 Hz), 151.84, 144.63 (br d, J=10.8 Hz), 130.95 (d, J=10.0 Hz), 130.97, 109.45 (d, J=2.3 Hz), 108.23 (d, J=21.6 Hz), 100.16 (d, J=26.2 Hz), 21.00. $^{19}F$ NMR (377 MHz, DMSO-$d_6$) δ=−111.71.

HRMS (ESI-TOF) m/z: $[M+H]^+$ Calcd for $C_{10}H_{11}FN_3O_2$ 224.0835. Found 224.0836.

Isomer 3:

$^1H$ NMR (400 MHz, DMSO-$d_6$) δ=11.85 (br s, 1H), 7.97 (d, J=8.4 Hz, 1H), 7.74 (d, J=8.4 Hz, 1H), 7.36-7.22 (m, 1H), 6.93-6.79 (m, 2H), 6.78-6.60 (m, 1H), 2.17 (s, 3H). $^{13}C$ NMR (101 MHz, DMSO-$d_6$) δ=167.91, 163.11 (br d, J=242.0 Hz), 155.53, 145.20 (br d, J=10.0 Hz), 131.66 (d, J=9.3 Hz), 126.80, 109.35 (d, J=2.3 Hz), 107.57 (d, J=21.6 Hz), 99.85 (d, J=27.0 Hz), 19.37. $^{19}F$ NMR (377 MHz, DMSO-$d_6$) δ=−111.95.

(E)-2-((E)-2-(2-(3-fluorophenyl)hydrazono)ethylidene)-1,1-dimethylhydrazine

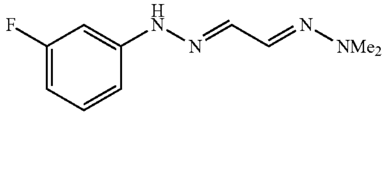

Yellow solid. mp: 134.4° C. (single isomer).

$^1H$ NMR (400 MHz, DMSO-$d_6$) δ=10.27 (s, 1H), 7.58 (d, J=7.9 Hz, 1H), 7.23-7.13 (m, 1H), 7.02 (d, J=8.1 Hz, 1H), 6.77-6.67 (m, 2H), 6.52-6.42 (m, 1H), 2.89 (s, 6H). $^{13}C$ NMR (101 MHz, DMSO-$d_6$) δ=163.33 (br d, J=240.4 Hz), 147.21 (d, J=10.8 Hz), 139.63, 130.69, 130.55 (d, J=10.0 Hz), 107.80 (d, J=1.5 Hz), 104.33 (d, J=21.6 Hz), 98.06 (d, J=26.2 Hz), 42.24. $^{19}F$ NMR (377 MHz, DMSO-$d_6$) δ=−112.61.

HRMS (ESI-TOF) m/z: $[M+H]^+$ Calcd for $C_{10}H_{14}FN_4$ 209.1202. Found 209.1200.

(1E,2E)-2-(2-(3-fluorophenyl)hydrazono)-N-(piperidin-1-yl)ethan-1-imine

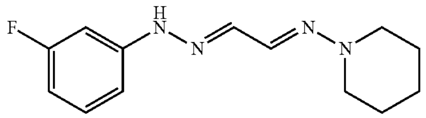 [SMILES: Fc1cccc(N/N=C/C=N/N2CCCCC2)c1]

Yellow solid. mp: 155.4° C. (single isomer).

$^1H$ NMR (400 MHz, DMSO-$d_6$) δ=10.36 (s, 1H), 7.58 (d, J=8.1 Hz, 1H), 7.31 (d, J=7.9 Hz, 1H), 7.25-7.08 (m, 1H), 6.83-6.62 (m, 2H), 6.48 (dt, J=2.3, 8.5 Hz, 1H), 3.06 (br t, J=5.4 Hz, 4H), 1.81-1.52 (m, 4H), 1.52-1.23 (m, 2H). $^{13}C$ NMR (101 MHz, DMSO-$d_6$) δ=163.31 (d, J=240.4 Hz, 1C), 147.05 (d, J=10.8 Hz, 1C), 139.45, 132.82, 130.55 (br d, J=10.0 Hz, 1C), 107.88 (br d, J=2.3 Hz, 1C), 104.54 (d, J=21.6 Hz, 1C), 98.17 (br d, J=26.2 Hz, 1C), 51.14, 24.43, 23.48. $^{19}F$ NMR (377 MHz, DMSO-$d_6$) δ=−112.59.

HRMS (ESI-TOF) m/z: $[M+H]^+$ Calcd for $C_{13}H_{18}FN_4$ 249.1515. Found 249.1518.

N'-((1E,2E)-2-(2-(3-fluorophenyl)hydrazono)ethylidene)acetohydrazide

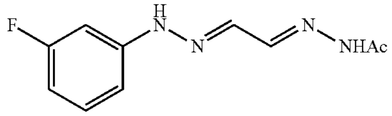 [SMILES: CC(=O)N/N=C/C=N/Nc1cccc(F)c1]

Yellow solid. mp: 265.1° C. (mixture of isomers).

Isomer 1 (Rotamer 1, Major):

$^1H$ NMR (400 MHz, DMSO-$d_6$) δ=11.22 (s, 1H), 10.85 (s, 1H), 7.75 (d, J=8.4 Hz, 1H), 7.57 (d, J=8.6 Hz, 1H), 7.25 (q, J=7.8 Hz, 1H), 6.93-6.73 (m, 2H), 6.59 (br t, J=7.8 Hz, 1H), 2.13 (s, 3H). $^{13}C$ NMR (101 MHz, DMSO-$d_6$) δ=190.43, 171.62, 163.26 (d, J=241.2 Hz, 1C), 146.20 (br d, J=10.8 Hz, 1C), 142.49, 136.15, 130.79 (d, J=10.0 Hz, 1C), 108.44 (d, J=2.3 Hz, 1C), 105.84 (br d, J=21.6 Hz, 1C), 98.86 (br d, J=26.2 Hz, 1C), 20.07. $^{19}F$ NMR (377 MHz, DMSO-$d_6$) δ=−112.21.

Isomer 1 (Rotamer 2, Minor):

$^1H$ NMR (400 MHz, DMSO-$d_6$) δ=11.37 (s, 1H), 10.92 (s, 1H), 7.87 (d, J=8.4 Hz, 1H), 7.62 (d, J=8.4 Hz, 1H), 7.25 (q, J=7.8 Hz, 1H), 6.93-6.73 (m, 2H), 6.59 (br t, J=7.8 Hz, 1H), 1.96 (s, 3H). $^{13}C$ NMR (101 MHz, DMSO-$d_6$) δ=190.43, 165.52, 163.26 (d, J=241.2 Hz, 1C), 146.17 (br d, J=10.8 Hz, 1C), 145.05, 136.32, 130.79 (d, J=10.0 Hz, 1C), 108.48 (br d, J=2.3 Hz, 1C), 105.91 (br d, J=21.6 Hz, 1C), 98.89 (br d, J=26.2 Hz, 1C), 21.56. $^{19}F$ NMR (377 MHz, DMSO-$d_6$) δ=−112.21.

HRMS (ESI-TOF) m/z: $[M+H]^+$ Calcd for $C_{10}H_{12}FN_4O$ 223.0995. Found 223.0994.

N'-((1E,2E)-2-(2-(3-fluorophenyl)hydrazono)ethylidene)-4-methylbenzenesulfonohydrazide

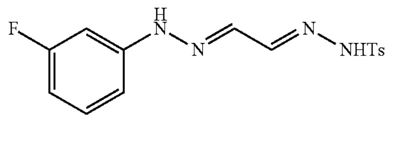

Yellow solid. mp: 146.7° C. (single isomer).

$^1H$ NMR (400 MHz, DMSO-$d_6$) δ=11.48 (s, 1H), 10.84 (s, 1H), 7.71 (d, J=8.4 Hz, 2H), 7.61 (d, J=8.4 Hz, 1H), 7.42 (br d, J=8.6 Hz, 1H), 7.41 (br d, J=8.1 Hz, 2H), 7.27-7.17 (m, 1H), 6.79-6.70 (m, 2H), 6.63-6.52 (m, 1H), 2.37 (s, 3H). $^{13}C$ NMR (101 MHz, DMSO-$d_6$) δ=163.18 (br d, J=241.2 Hz), 146.37, 145.99 (br d, J=10.8 Hz), 143.46, 136.07, 135.31, 130.83 (d, J=10.0 Hz), 129.68, 127.05, 108.52 (d, J=2.3 Hz), 106.07 (d, J=21.6 Hz), 98.92 (d, J=26.2 Hz), 20.96. $^{19}F$ NMR (377 MHz, DMSO-$d_6$) δ=−112.20.

HRMS (ESI-TOF) m/z: $[M+H]^+$ Calcd for $C_{15}H_{16}FN_4O_2S$ 335.0978. Found 335.0982.

(E)-2-((E)-2-(2-(3-fluorophenyl)hydrazono)ethylidene)-1,1,1-trimethylhydrazin-1-ium iodide

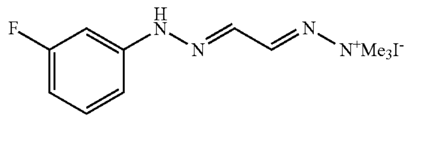

To a solution of (E)-2-(2-(3-fluorophenyl)hydrazono)acetaldehyde (1 mmol, 1.0 eq.) and NaOAc (1.5 mmol, 1.5 eq.) in MeOH (3 mL) 1,1-dimethylhydrazine hydrochloride salt (1.2 mmol, 1.2 eq.) was added in one portion at 25° C. After consumption of the starting material (ca 30 min), water (3 mL) was added into the reaction mixture. The suspension was then filtered and the cake was washed with water. The intermediate dihydrazone (E)-2-((E)-2-(2-(3-fluorophenyl) hydrazono)ethylidene)-1,1-dimethylhydrazine was dried under vacuum at 50° C. for 3 h. To a solution of the so-obtained (E)-2-((E)-2-(2-(3-fluorophenyl)hydrazono) ethylidene)-1,1-dimethylhydrazine (1.0 mmol, 1.0 eq.) (either isolated or non-isolated intermediate) in ACN (2 mL) was added MeI (5.0 mmol, 5.0 eq.) in one portion at 25° C. After overnight stirring or until the consumption of the starting material, EtOAc (3 mL) was added into the suspension. The suspension was filtered the cake was washed with EtOAc. The hydrazonium salt (E)-2-((E)-2-(2-(3-fluorophenyl)hydrazono)ethylidene)-1,1,1-trimethylhydrazin-1-ium iodide was dried under vacuum at 30° C. to deliver 315 mg of yellow solid (yield: 90%).

mp: 166.8° C.

$^1H$ NMR (400 MHz, DMSO-$d_6$): δ 11.82 (s, 1H), 8.73 (d, J=8.0 Hz, 1H), 7.63 (d, J=8.1 Hz, 1H), 7.35 (dd, J=15.1, 8.2 Hz, 1H), 6.99-6.90 (m, 2H), 6.82-6.71 (m, 1H), 3.47 (s, 9H). $^{13}C$ NMR (101 MHz, DMSO-$d_6$): δ 164.73, 163.18, 162.32, 145.32, 145.22, 131.81, 131.72, 131.12, 110.01, 108.77, 108.56, 100.55, 100.29, 55.52, 55.46.

HRMS (ESI) calcd. for $C_{11}H_{16}FN_4^+$ $[M^+]$: 223.1359, found: 223.1348. M.P.: 166.8° C.

Example 2d: Synthesis of methyl 2-fluoro-6-(2-(2-(methoxyimino)ethylidene)hydrazinyl)benzoate

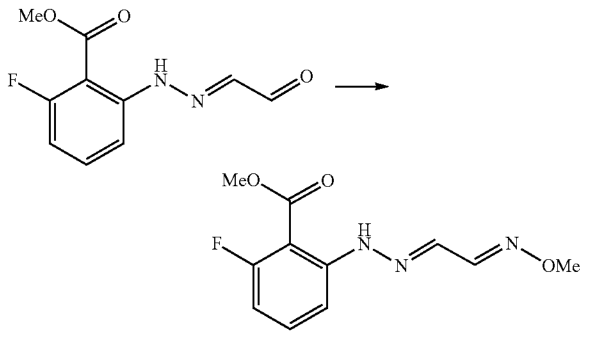

A solution of methoxylamine hydrochloride (3.61 g, 43.2 mmol) and sodium acetate (3.55 g, 43.2 mmol) in water (80 ml) was added to a solution of methyl (E)-2-fluoro-6-(2-(2-oxoethylidene)hydrazinyl)benzoate (8.07 g, 36.0 mmol) in methanol (40 ml). after overnight stirring at room temperature, the title compound was filtered, rinsed with water (2×15 ml) and dried under vacuum. The desired product (7.85 g, 79% yield) was obtained as a yellow solid. NMR shows the presence of several isomers. mp 90.0° C.

$^1H$ NMR (DMSO-$d_6$-major isomer) δ: 10.87 (s, 1H), 7.76 (m, 2H), 7.40 (m, 1H), 7.11 (m, 1H), 6.72 (m, 1H), 3.86 (s, 3H), 3.83 (s, 3H).

MS (ESI-TOF) m/z: 254.2 ($[M+H]^+$).

Example 2e: Synthesis of (E)-2-((E)-2-(2-(3-fluoro-2-(methoxycarbonyl)phenyl)hydrazineylidene)ethylidene)-1,1,1-trimethylhydrazin-1-ium iodide

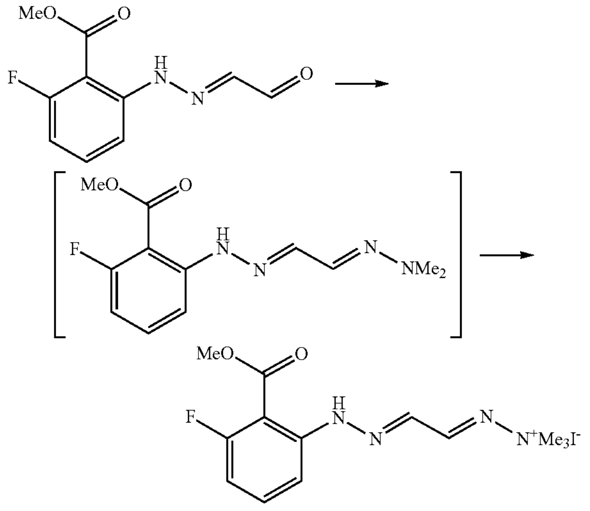

A suspension of 1,1-dimethylhydrazine hydrochloride (0.76 g, 7.9 mmol) and sodium acetate (0.74 g, 9.0 mmol) in methanol (10 ml) was added slowly to a solution of methyl (E)-2-fluoro-6-(2-(2-oxoethylidene)hydrazinyl)benzoate (1.68 g, 7.5 mmol) in toluene-methanol (25 ml+6 ml). after 1 h stirring at room temperature, the mixture was concentrated under vacuum and the residue was partitioned between water and ethyl acetate (10 ml+20 ml). after phase separation, the aqueous layer was extracted with ethyl acetate (20 ml) and the combined organic layers were concentrated under vacuum. The resulting oil was purified by chromatography (silica gel, eluent: ethyl acetate—heptane, ⅛) and the intermediate dihydrazone (1.8 g) was obtained as a yellow solid. The intermediate (1.6 g) was then redissolved in acetonitrile (12 ml), iodomethane (5.11 g, 36.0 mmol) was added and the reaction mixture was stirred at 36° C. for 8 h. after cooling to room temperature, the solid was filtered, rinsed with acetonitrile (2×20 ml) and dried under vacuum to deliver the desired compound (2.0 g, 65% overall yield) as a yellow solid. mp: 177.5° C.

$^1H$ NMR (DMSO-$d_6$) δ: 11.51 (s, 1H), 8.57 (d, 1H), 7.84 (m, 2H), 7.50 (m, 1H), 7.25 (m, 1H), 6.88 (m, 1H), 3.86 (s, 3H), 3.45 (s, 9H). $^{19}F$ NMR (DMSO-$d_6$) δ: −111.49.

MS (ESI-TOF) m/z: 281.1 ([hydrazonium ion]$^+$).

Example 2f: Synthesis of 2-fluoro-6-(2-41E,2E)-2-(methoxyimino)ethylidene)hydrazinyl)benzoic Acid

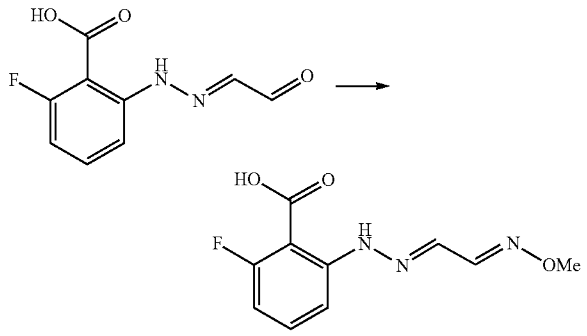

2-fluoro-6-(2-(2-oxoethylidene)hydrazinyl)benzoic acid was allowed to react with methoxylamine hydrochloride and sodium acetate in water-methanol to deliver 2-fluoro-6-(2-((1E,2E)-2-(methoxyimino)ethylidene)hydrazinyl)benzoic acid in 52% yield as a yellow solid. the desired compound was used as such in the next step.

Example 3: Synthesis of 2-phenyl-2H-1,2,3-triazoles of Formula II

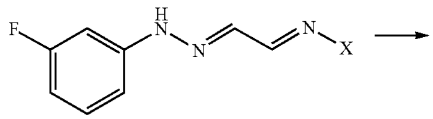

-continued

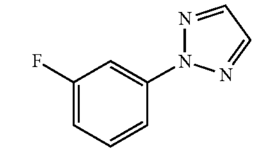

Example 3a: Synthesis of 2-(3-fluorophenyl)-2H-1,2,3-triazole, where X is —$N^+Me_3I^-$ To a solution of hydrazonium salt (E)-2-((E)-2-(2-(3-fluorophenyl)hydrazono)ethylidene)-1,1,1-trimethylhydrazin-1-ium iodide (X=—$N^+Me_3I^-$–1.0 mmol, 1.0 eq.) in DMF (3 mL) was added $K_2CO_3$ or $KHCO_3$ (2.0 mmol, 2.0 eq.) in one portion at 25° C. The suspension was heated to 50° C. After stirring for 2 h or until the consumption of the starting material, the reaction was cooled to 25° C. and treated with $H_2O$ and EtOAc. The organic layer was partitioned and extracted with EtOAc twice. The combined organics were washed with brine, dried over $Na_2SO_4$, filtered and concentrated under vacuum. Purification by flash column chromatography using heptane/ethyl acetate as eluents afforded 2-(3-fluorophenyl)-2H-1,2,3-triazole in 87% yield.

Yield was improved to 96% when $K_2CO_3$ was replaced by $KHCO_3$.

Example 3b: Synthesis of 2-(3-fluorophenyl)-2H-1,2,3-triazole Using Other —X Groups Synthesis of 2-(3-fluorophenyl)-2H-1,2,3-triazole from compounds of Formula I where $R^1$ is H may be accomplished for a variety of —X leaving groups following the procedure below:

A solution/suspension of 5 mmol of a compound of Formula I where $R^1$ is H and of 0.25 mmol of copper sulfate pentahydrate or copper mesylate hydrate in 5 to 7 mL of n-butanol or of ethylene glycol (EG) was stirred several hours at 110° C. before being cooled to room temperature, washed with 7.5 ml of aqueous 1M HCl, and assayed by LC for 2-(3-fluorophenyl)-2H-1,2,3-triazole.

The following Table 2 illustrates yields obtained for each —X leaving group under the conditions listed. Reaction conditions are not optimized, and the invention contemplates reaction conditions for each —X group, as well as obvious variants thereof. An example of various screening conditions that may be used for reaction optimization for any —X leaving group is shown for example 3c, where —X is —$OCH_3$.

TABLE 2

| Leaving Group-X | Conditions, (copper salt, solvent) | % In-situ yield 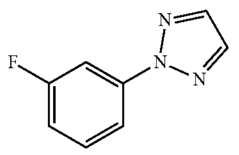 [SMILES: Fc1cccc(-n2nccn2)c1] |
|---|---|---|
| —OMe | $CuSo_4$•$5H_2O$, n-butanol | 70 |
| —OH | $CuSO_4$•$5H_2O$, ethylene glycol | 28 |

TABLE 2-continued

| Leaving Group-X | Conditions, (copper salt, solvent) | % In-situ yield 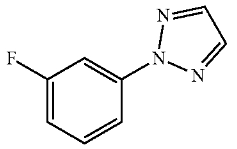 |
|---|---|---|
| —OEt | $CuSO_4$•$5H_2O$, n-butanol | 70 |
| —OtBu | $CuSO_4$•$5H_2O$, ethylene glycol | 41 |
| —OtBu | copper mesylate, n-butanol | 54 |
| —OBn | $CuSO_4$•$5H_2O$, n-butanol | 54 |
| —OPh | $CuSO_4$•$5H_2O$, n-butanol | 18 |
| —OAc | $CuSO_4$•$5H_2O$, n-butanol | 20 |
| —OMs | $CuSO_4$•$5H_2O$, ethylene glycol | 0 |
| —$NMe_2$ | $CuSO_4$•$5H_2O$, ethylene glycol | 50 |
| 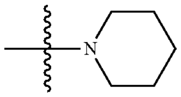 [SMILES: *N1CCCCC1] | $CuSO_4$•$5H_2O$, ethylene glycol | 32 |
| —NHAc | $CuSO_4$•$5H_2O$, ethylene glycol | 25 |
| —NHTs | $CuSO_4$•$5H_2O$, ethylene glycol | 4 |

Example 3c: Synthesis of 2-(3-fluorophenyl)-2H-1,2,3-triazole from (1E,2E)-2-(2-(3-fluorophenyl)hydrazono)acetaldehyde O-methyl oxime (Screening of Conditions)

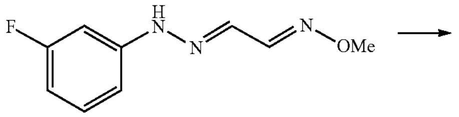

-continued

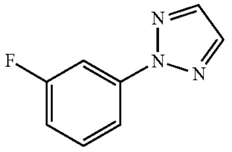

A solution of (1E,2E)-2-(2-(3-fluorophenyl)hydrazono) acetaldehyde O-methyl oxime (1 equiv) and catalyst in a solvent was heated at 110° C. — 120° C. for 20 min—overnight before cooling to room temperature and LC-assay for 2-(3-fluorophenyl)-2H-1,2,3-triazole. Reaction conditions and yields are summarized in Table 3.

TABLE 3

| Conditions | Time to completion | Isolated yield |
|---|---|---|
| $CuSO_4$ (5 mol %), EG (5 L/kg), 120° C. | 40 min | 60% |
| $CuSO_4$ (5 mol %), EG (3 L/kg), 120° C. | 40 min | 64% |
| $CuSO_4$ (5 mol %), EG (10 L/kg), 120° C. | 65 min | 68% |
| $CuSO_4$ (5 mol %), MeOH (5 L/kg), 66° C. (rfx) | 13 days | — |
| $CuSO_4$ (5 mol %), MeOH (5 L/kg), 120° C. (MW, overpressure) | 50 h | 80% |
| $CuSO_4$ (5 mol %), n-BuOH (5 L/kg), 110° C. | 2 h | 82% |
| $Cu(OTf)_2$ (5 mol %), EG (5 L/kg), 120° C. | 1 h 20 | 40% |
| $Cu(OTf)_2$ (5 mol %), toluene (5 L/kg), 100° C. | 160 h | 71% |
| $Cu(OTf)_2$ (5 mol %), DMF (5 L/kg), 120° C. | 160 h | 53% |
| $Cu(OMs)_2$ (5 mol %), n-BuOH (5 L/kg), 110° C. | 1 h, 30 min | 86% |
| CuOTf (5 mol %), n-BuOH (5 L/kg), 110° C. | 2 h, 30 min | 73% |
| $Cu(OTf)_2$ (5 mol %), n-BuOH (5 L/kg), 110° C. | 3 h, 30 min | 55% |
| CuOAc (5 mol %), n-BuOH (5 L/kg), 110° C. | 20 min | 66% |
| $Cu(OAc)_2$ (5 mol %), n-BuOH (5 L/kg), 110° C. | 20 min | 72% |
| $Ni(OAc)_2$ (5 mol %), n-BuOH (5 L/kg), 110° C. | 24 h | — |
| $Zn(OAc)_2$ (5 mol %), n-BuOH (5 L/kg), 110° C. | 24 h | — |
| Au(I) complexe (5 mol %), n-BuOH (5 L/kg), 110° C. | 24 h | — |
| EG (5 L/kg), $CH_3SO_3H$ (1 equiv), 120° C. | 24 h | degradation |
| EG (5 L/kg), $K_2CO_3$ (1 equiv), 120° C. | 24 h | degradation |
| EG (5 L/kg), MeONa (1 equiv), 120° C. | 24 h | degradation |
| DMF (5 L/kg), $K_2CO_3$ (1 equiv), 120° C. | 24 h | <5% product |

Example 3d: Formation and isolation of 2-(3-fluorophenyl)-2H-1,2,3-triazole from (1E,2E)-2-(2-(3-fluorophenyl)hydrazono)acetaldehyde O-methyl oxime A reactor was charged with 0.31 kg of copper sulfate pentahydrate and 26.8 kg of EG, made inert and heated to 120-130° C. with stirring. 4.8 kg of (1E,2E)-2-(2-(3-fluorophenyl)hydrazono)acetaldehyde O-methyl oxime was added in 5 portions. After 1 hour of stirring at 120-130° C., part of the reaction mixture was distilled under vacuum. The distillate (13 L, 2-(3-fluorophenyl)-2H-1,2,3-triazole+EG) was partitioned between 3.3 kg of heptane and 4.8 kg of 2 w/w % aqueous HCl. The two layers were separated and the polar one, extracted with 3.3 kg of heptane. The two heptane layers were combined, washed with 4.8 kg of water and concentrated under vacuum to deliver 3.09 kg of 2-(3-fluorophenyl)-2H-1,2,3-triazole as colorless to slightly yellow oil (yield: 77%).

$^1$H NMR (400 MHz, DMSO-$d_6$) δ=8.14 (s, 2H), 7.87 (dd, J=1.3, 8.1 Hz, 1H), 7.79 (td, J=2.2, 10.1 Hz, 1H), 7.60 (dt, J=6.4, 8.3 Hz, 1H), 7.26 (ddt, J=0.9, 2.5, 8.5 Hz, 1H). $^{13}$C NMR (101 MHz, DMSO-$d_6$) δ=162.38 (br d, J=244.3 Hz), 140.32 (d, J=1.5 Hz), 136.88, 131.63 (d, J=9.2 Hz), 114.34 (d, J=3.1 Hz), 114.37 (d, J=20.8 Hz), 105.79 (d, J=27.7 Hz). $^{19}$F NMR (377 MHz, DMSO-$d_6$) δ=−110.88.

HRMS (EI-TOF) m/z: $[M]^{+o}$ Calcd for $C_8H_6FN_3$ 163.0546. Found 163.0521.

Example 3e part 1: Synthesis of methyl 2-fluoro-6-(2H-1,2,3-triazol-2-yl)benzoate from methyl 2-fluoro-6-(2-(2-(methoxyimino)ethylidene)hydrazineyl)benzoate

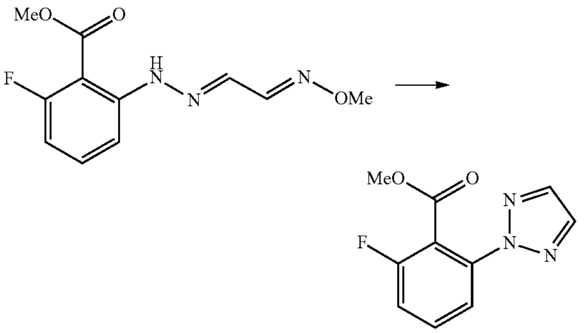

Methyl 2-fluoro-6-(2-(2-(methoxyimino)ethylidene)hydrazineyl)benzoate (4.05 g, 16 mmol) was added in four portions to a solution of copper sulfate pentahydrate (250 mg, 1.0 mmol) in ethylene glycol (25 ml) kept at 125° C. The resulting mixture was stirred at 125° C. for 3 hours longer before being cooled down to 60° C. Water (60 ml), heptane (30 ml) and ethyl acetate (20 ml) were added and the layers were separated. 1.3 g (37% yield) of the desired product was obtained after concentration of the organic layer and purification of the residue by column chromatography (silica gel, heptane-ethyl acetate 8/1). mp 56.9° C.

Yield of methyl 2-fluoro-6-(2H-1,2,3-triazol-2-yl)benzoate was improved to 54% when methyl 2-fluoro-6-(2-(2-(methoxyimino)ethylidene)hydrazineyl)benzoate (633 mg, 2.50 mmol) and copper sulfate pentahydrate (31 mg, 0.125 mmol) were first mixed in ethylene glycol (5 ml) at room temperature then heated to 120° C. (full dissolution of the chemicals was obtained upon heating) for about 4 hours before cooling to room temperature, dilution with water, extraction with isopropyl acetate and purification by column chromatography. Yield of 57% yield was obtained when the above procedure was repeated with 1.00 mmol of starting material, 0.05 mmol of copper sulfate pentahydrate in 10 ml of ethylene glycol, and with a heating time of about 8 hours.

$^1$H NMR (DMSO-$d_6$) δ: 8.18 (s, 2H), 7.87 (d, 1H), 7.75 (m, 1H), 7.48 (t, 1H), 3.78 (s, 3H). $^{13}$C NMR (DMSO-$d_6$) δ: 163.68, 159.40 (d), 137.63, 137.6 (d), 133.27 (d), 118.00 (d), 115.86 (d), 115.8 (d), 53.28. $^{19}$F NMR (DMSO-$d_6$) δ: −114.28.

Example 3e part 2: Synthesis of 2-fluoro-6-(2H-1,2,3-triazol-2-yl)benzoic acid from methyl 2-fluoro-6-(2H-1,2,3-triazol-2-yl)benzoate

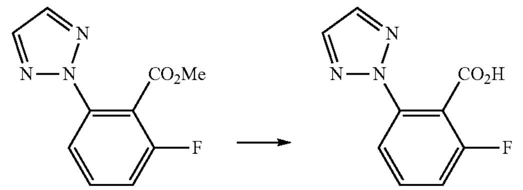 [SMILES: COC(=O)c1c(F)cccc1-n1nccn1 ; O=C(O)c1c(F)cccc1-n1nccn1]

A solution of methyl 2-fluoro-6-(2H-1,2,3-triazol-2-yl)benzoate (360 mg) and lithium hydroxide hydrate (66 mg, 10.2 mmol) in THF-water (2 ml each) was stirred until complete conversion. The desired product was obtained in 86% yield after neutralization and isolation.

Example 3f: Synthesis of methyl 2-fluoro-6-(2H-1,2,3-triazol-2-yl)benzoate from (E)-2-4E)-2-(2-(3-fluorophenyl)hydrazono)ethylidene)-1,1,1-trimethylhydrazin-1-ium iodide

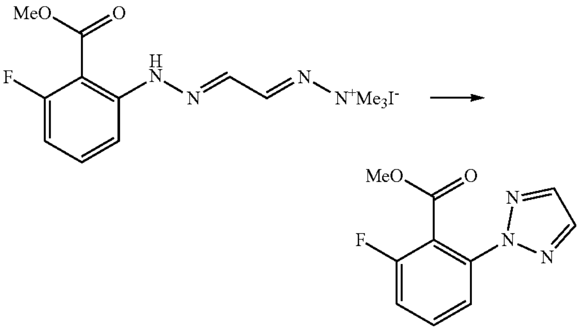

A solution of methyl 2-fluoro-6-(2H-1,2,3-triazol-2-yl)benzoate from (E)-2-((E)-2-(2-(3-fluorophenyl)hydrazono)ethylidene)-1,1,1-trimethylhydrazin-1-ium iodide (0.61 g, 1.5 mmol) and potassium bicarbonate (0.75 g, 7.5 mmol) in DMF (10 ml) was stirred at 56° C. for 1 h before concentration under vacuum. The residue was partitioned between heptane and water (15 ml+6 ml). After phase separation, the aqueous layer was extracted with heptane (15 ml) and the combined organic layers were concentrated under vacuum to deliver the desired product (0.27 g, 81% yield) as a yellow powder.

Example 3g: Synthesis of 2-fluoro-6-(2H-1,2,3-triazol-2-yl)benzoic acid from 2-fluoro-6-(2-41E, 2E)-2-(methoxyimino)ethylidene)hydrazinyl)benzoic Acid

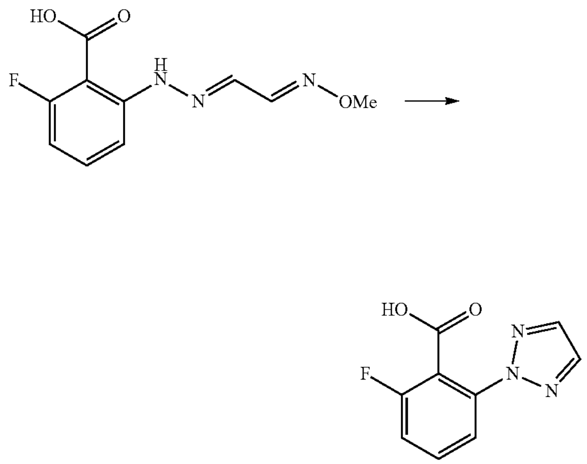 [SMILES: CO/N=C/C=N/Nc1cccc(F)c1C(=O)O ; O=C(O)c1c(F)cccc1-n1nccn1]

2-Fluoro-6-(2-((1E,2E)-2-(methoxyimino)ethylidene)hydrazinyl)benzoic acid was allowed to react in the presence of copper sulfate pentahydrate in warm ethylene glycol to deliver 2-fluoro-6-(2H-1,2,3-triazol-2-yl)benzoic acid in about 25% yield.

Example 4: Synthesis of 2-fluoro-6-(2H-1,2,3-triazol-2-yl)benzoic acid from 2-(3-fluorophenyl)-2H-1,2,3-triazole

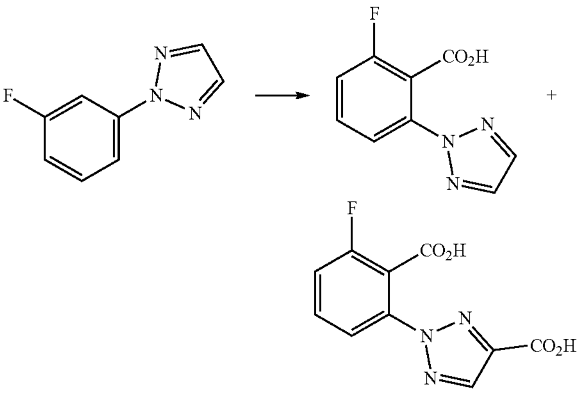

Example 4a: Screening of Bases and Additives

A base was added to a solution of Compound 2-(3-fluorophenyl)-2H-1,2,3-triazole and the mixture was stirred before bubbling of $CO_2$ gas until complete quench of the anion and acidic workup. The resulting mixture was analyzed by LC and 2-fluoro-6-(2H-1,2,3-triazol-2-yl)benzoic acid was isolated after completion of the workup. Results are reported in Table 4 below.

TABLE 4

| | Mixture after quench, LC (area %) | | | |
|---|---|---|---|---|
| Conditions | 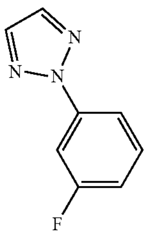 [SMILES: Fc1cccc(-n2nccn2)c1] | 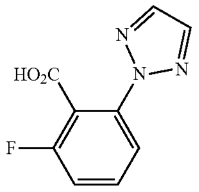 [SMILES: O=C(O)c1c(F)cccc1-n1nccn1] | 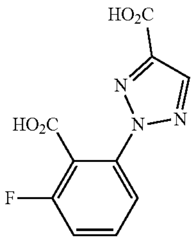 [SMILES: O=C(O)c1cnn(-c2cccc(F)c2C(=O)O)n1] | yield % |
| iPrMgCl (1.2 equiv), THF, 35-40° C. then $CO_2$ (1.3 equiv), −5° C. Workup: toluene-aq HCl. Isolation: solvent switch → toluene-water, reflux to 25° C. | 1.5 | 95.3 | 1.4 | 78 |
| iPrMgCl (1.2 equiv), LiCl (0.5 equiv), THF, 35-40° C. then $CO_2$ (1.3 equiv), −5° C. Workup: toluene-aq HCl. Isolation: solvent switch → toluene-water, reflux to 25° C. | 5.7 | 93.1 | 0.3 | 87 |
| iPrMgCl (1.2 equiv), LiCl (1 equiv), THF, 35-40° C. then $CO_2$ (1.3 equiv), −5° C. Workup: toluene-aq HCl. Isolation: solvent switch → toluene-water, reflux to 25° C. | 14.8 | 84.4 | 0.2 | 78 |

Example 4b: Synthesis and isolation of 2-fluoro-6-(2H-1,2,3-triazol-2-yl)benzoic Acid A solution of 2M isopropylmagnesium chloride solution in THF (735 mL, 1.47 mol) was added to a heated (35-40° C.) solution of 200 g (1.23 mol) of 2-(3-fluorophenyl)-2H-1,2,3-triazole and 25.98 g (0.61 mol) of lithium chloride in one liter of THF. The resulting mixture was stirred for 6 hours at 35-40° C. before being cooled to −5° C. $CO_2$ gas (67.44 g, 1.53 mol) was bubbled through the mixture at a rate that did not allow the reaction temperature to exceed 10° C. The reaction mixture was quenched by the addition of 800 mL toluene, 800 mL water, and 144 mL of concentrated HCl solution. After dissolution of insoluble particles, the two layers were separated, and the aqueous layer was discarded. The organic layer was filtered through charcoal and concentrated under vacuum before redissolution of the residue in 1.80 L of toluene and 800 mL of water; the biphasic mixture was heated to reflux for a few minutes, cooled to 75-80° C., seeded, and cooled further to 10° C. After crystallization, the product was isolated by filtration, washed with a few mL of water and of toluene and dried under vacuum to obtain 2-fluoro-6-(2H-1,2,3-triazol-2-yl)benzoic acid (212-217 g, 83-85% yield) of white to light yellow solid.

mp 153-155° C.

$^1$H NMR (400 MHz, DMSO-$d_6$) δ=13.70 (br s, 1H), 8.14 (s, 2H), 7.79 (d, J=8.1 Hz, 1H), 7.66 (dt, J=6.1, 8.3 Hz, 1H), 7.42 (ddd, J=1.0, 8.4, 9.3 Hz, 1H). $^{13}$C NMR (101 MHz, DMSO-$d_6$) δ=164.09, 158.90 (br d, J=247.4 Hz), 136.97, 136.77 (br d, J=6.2 Hz), 131.82 (d, J=9.2 Hz), 118.03 (d, J=3.1 Hz), 117.25 (br d, J=23.1 Hz), 115.48 (d, J=22.3 Hz). $^{19}$F NMR (377 MHz, DMSO-$d_6$) δ=−114.93.

HRMS (ESI-TOF) m/z: $[M+H]^+$ Calcd for $C_9H_7FN_3O_2$ 208.0517. Found 208.0517.

Example 5: Synthesis of (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

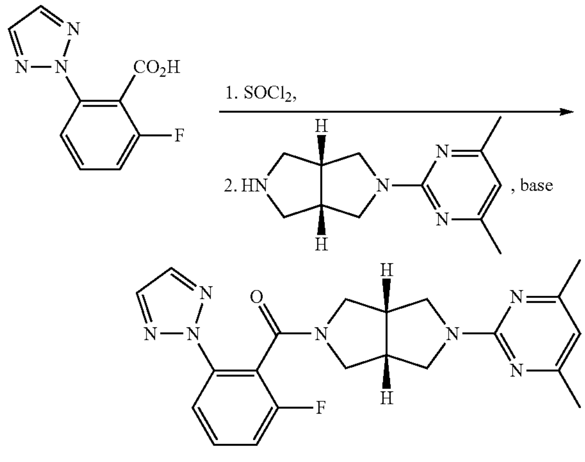

Seltorexant

Thionyl chloride (60 mmol, 4.3 mL) was added to a suspension of 2-fluoro-6-(2H-1,2,3-triazol-2-yl)benzoic acid (9.5 g, 46 mmol) in toluene (110 mL) and heated to 55° C. for 2.5 hours. The reaction was concentrated under vacuum to a residual volume of about 100 mL (about 20 ml of solvent distilled) and added to a well stirred biphasic mixture of (3aR,6aS)-2-(4,6-dimethylpyrimidin-2-yl)octahydropyrrolo[3,4-c]pyrrole (10.2 g, 45.7 mmol) in toluene (44 mL) and aqueous sodium carbonate (44 mL, 68.5 mmol). The resulting biphasic mixture was stirred at 30° C. for 3.5 hours before being heating to 70° C. The organic layer was washed twice with 57 mL of water and concentrated under vacuum to a residual volume of about 64 mL. The concentrated mixture was heated to 90° C. to obtain a solution before cooling to room temperature and addition of cyclohexane (64 mL). The resulting suspension was stirred overnight, filtered, washed with cyclohexane (12 mL), washed with water (11 mL), and dried under vacuum to give (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone (18.1 g, 97% yield) as a solid. $^1$H NMR (400 MHz, pyridine-$d_5$) δ ppm 2.33 (s, 12H) 2.81-2.97 (m, 4H) 3.27 (dd, J=10.6, 5.0 Hz, 1H) 3.33 (dd, J=10.5, 4.7 Hz, 1H) 3.57 (br t, J=7.1 Hz, 1H) 3.59 (br t, J=7.0 Hz, 1H) 3.67 (dd, J=11.7, 4.5 Hz, 1H) 3.70-3.75 (m, 1H) 3.75-3.82 (m, 2H) 3.82-3.98 (m, 7H) 4.11 (dd, J=12.4, 7.6 Hz, 1H) 6.29 (s, 1H) 6.29 (s, 1H) 7.19 (td, J=8.7, 1.0 Hz, 1H) 7.26 (td, J=8.6, 0.9 Hz, 1H) 7.46 (td, J=8.3, 6.2 Hz, 1H) 7.46 (td, J=8.3, 6.0 Hz, 1H) 7.90 (dt, J=8.2, 0.8 Hz, 1H) 7.90 (s, 2H) 7.98 (dt, J=8.2, 0.8 Hz, 1H) 8.04 (s, 2H). $^{13}$C NMR (101 MHz, pyridine-$d_5$) δ ppm 24.47, 24.48, 41.74, 41.82, 42.71, 42.93, 50.76, 50.82, 50.90, 51.03, 51.43, 51.62, 51.87, 52.06, 109.27, 109.44, 115.88 (br d, J=22.4 Hz), 115.89 (br d, J=22.4 Hz), 118.82 (br d, J=3.3 Hz), 118.97 (br d, J=3.3 Hz), 120.48 (d, J=24.9 Hz), 120.55 (d, J=24.6 Hz), 131.53 (br d, J=9.2 Hz), 131.54 (d, J=9.2 Hz), 137.33, 137.47, 138.04 (d, J=7.0 Hz), 138.07 (br d, J=7.0 Hz), 159.71 (d, J=245.8 Hz), 159.81 (d, J=245.4 Hz), 161.53, 161.61, 162.99 (d, J=7.3 Hz), 162.99 (d, J=7.3 Hz), 167.61, 167.63. High resolution MS (ES, m/z): calcd for $C_{21}H_{23}FN_7O$ $(M+H)^+$: 408.1943; found: 408.1946.

While the foregoing specification teaches the principles of the present invention, with examples provided for the purpose of illustration, it will be understood that the practice of the invention encompasses all of the usual variations, adaptations and/or modifications as come within the scope of the following claims and their equivalents. All documents cited herein are incorporated by reference.

What is claimed is:

1. A process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone:

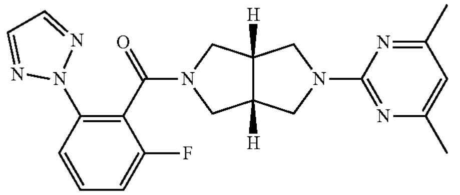 [SMILES: Cc1cc(C)nc(N2C[C@H]3CN(C(=O)c4c(F)cccc4-n4nccn4)C[C@H]3C2)n1]

said process comprising step described below:

cyclization of a hydrazine of Formula I to give a 2-phenyl-2H-1,2,3-triazole of Formula II in a single step:

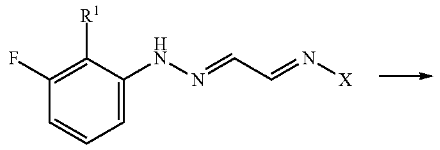

I

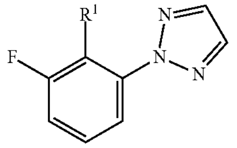

II wherein:

$R^1$ is —H, —$CO_2H$, or —$CO_2C_{(1-4)}$alkyl; and

X is —$OC_{(1-2)}$alkyl, —$OCH_2Ph$, $OC(CH_3)_3$, —$N(CH_3)_2$, or —$N(CH_3)_3I$.

2. The process of claim 1, wherein $R^1$ is —H, or —$CO_2CH_3$.

3. The process of claim 2, said process comprising the steps described below:

a) cyclization of the hydrazine of Formula I to give the 2-phenyl-2H-1,2,3-triazole of Formula II in a single step:

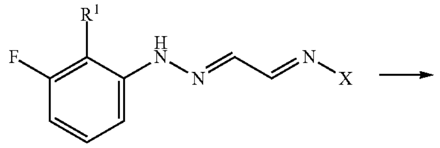

I

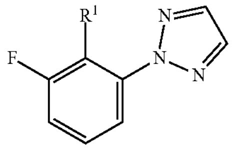

II wherein:

$R^1$ is —H; and b) carboxylation of 2-(3-fluorophenyl)-2H-1,2,3-triazole to give 2-fluoro-6-(2H-1,2,3-triazol-2-yl)benzoic acid:

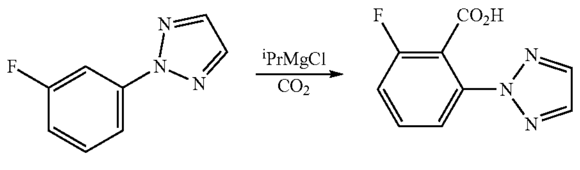

wherein said carboxylation is characterized by the use of isopropyl-MgCl and $CO_2$.

4. The process of claim 3, said process comprising the steps described below:

a) cyclization of the hydrazine of Formula I to give the 2-phenyl-2H-1,2,3-triazole of Formula II in a single step:

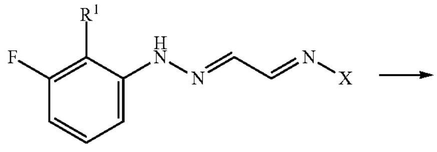

I

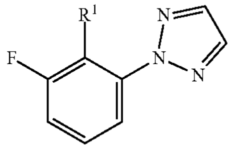

II b) carboxylation of 2-(3-fluorophenyl)-2H-1,2,3-triazole to give 2-fluoro-6-(2H-1,2,3-triazol-2-yl)benzoic acid:

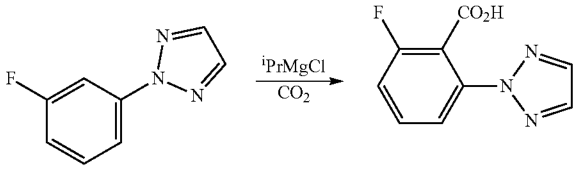

wherein said carboxylation is characterized by the use of isopropyl-MgCl and $CO_2$; and c) reaction of 2-fluoro-6-(2H-1,2,3-triazol-2-yl)benzoic acid with (3aR,6aS)-2-(4,6-dimethylpyrimidin-2-yl)octahydropyrrolo[3,4-c]pyrrole to form (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone:

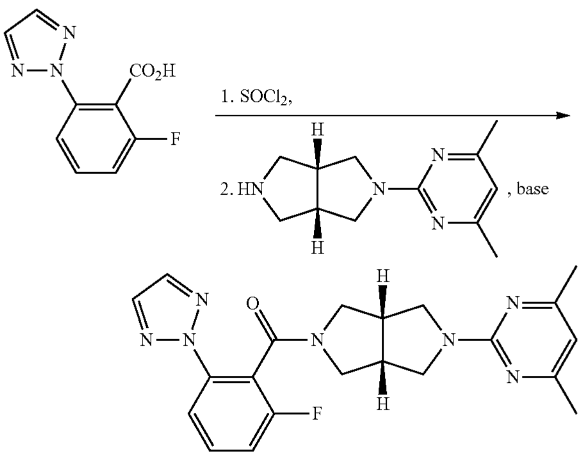

wherein said reaction is characterized by the use of $SOCl_2$.

5. The process of claim 4, said process comprising the steps described below:

a) cyclization of the hydrazine of Formula I to give the 2-phenyl-2H-1,2,3-triazole of Formula II in a single step:

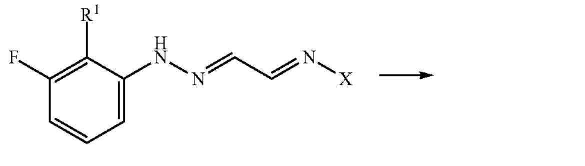

I

II b) carboxylation of 2-(3-fluorophenyl)-2H-1,2,3-triazole to give 2-fluoro-6-(2H-1,2,3-triazol-2-yl)benzoic acid:

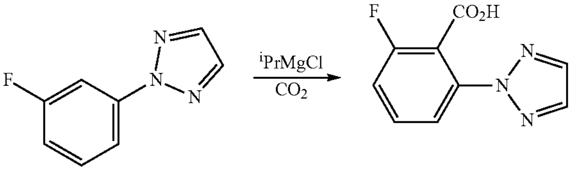

wherein said carboxylation is characterized by the use of LiCl, isopropyl-MgCl and $CO_2$; and c) reaction of 2-fluoro-6-(2H-1,2,3-triazol-2-yl)benzoic acid with (3aR,6aS)-2-(4,6-dimethylpyrimidin-2-yl)octahydropyrrolo[3,4-c]pyrrole to form (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone:

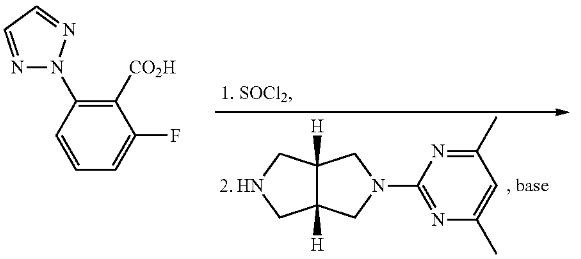

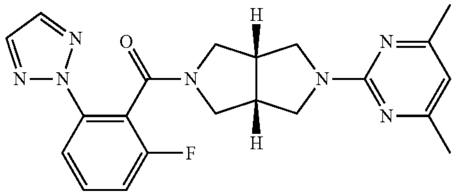

wherein said reaction is characterized by the use of $SOCl_2$.

6. A method of making a compound of Formula I:

I

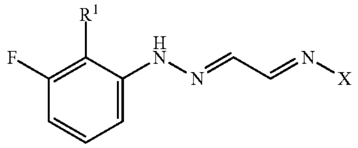

said method comprises:

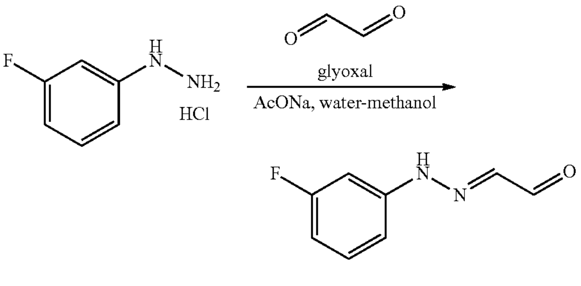

reaction of (3-fluorophenyl) hydrazine hydrochloride with glyoxal, in the presence of water and/or methanol, to form (E)-2-(2-(3-fluorophenyl)hydrazono)acetaldehyde in over 90% yield;

wherein:

$R^1$ is H, $CO_2H$, or $—CO_2C_{(1-4)}$alkyl; and

X is $—OC_{(1-2)}$alkyl, $—OC(CH_3)_3$, $—OCH_2Ph$, $—N(CH_3)_2$, or $—N(CH_3)_3I$.

7. A compound of Formula III:

III

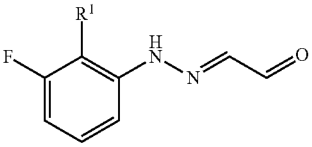

wherein $R^1$ is H, $CO_2H$, or $—CO_2C_{(1-4)}$alkyl.

8. The compound of claim 7 selected from the group consisting of:

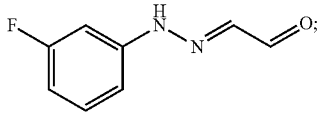

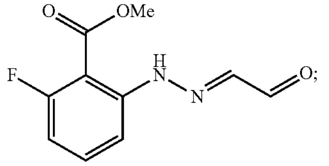

and

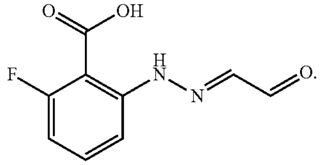

9. A compound selected from the group consisting of:
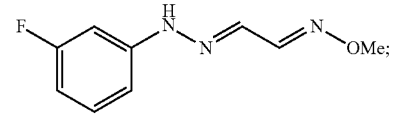
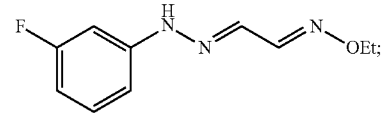
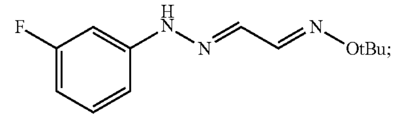
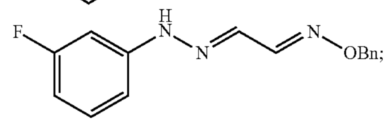
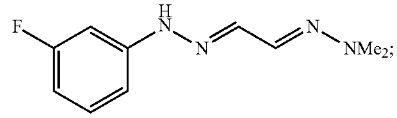
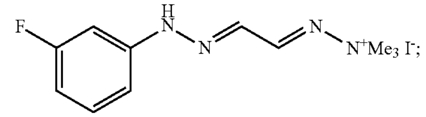
-continued
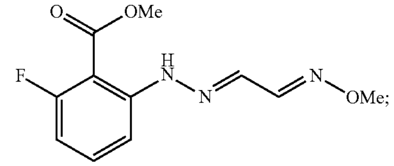
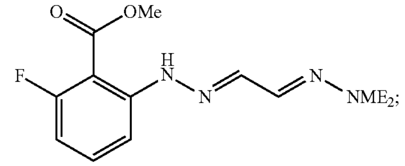
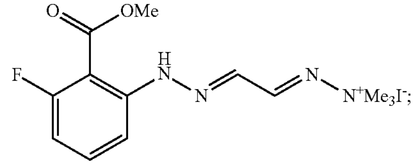
and
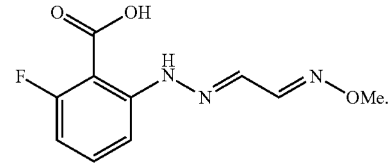
* * * * *